US012802783B2

(12) United States Patent
Shcherbakov et al.

(10) Patent No.: US 12,802,783 B2
(45) Date of Patent: Nov. 17, 2026

(54) FRAGRANCE INGREDIENT SPATIAL RECOGNISABILITY PREDICTION METHODS AND FRAGRANCE COMPOSITION SPATIAL RECOGNISABILITY PREDICTION METHODS

(71) Applicant: Firmenich SA, Satigny (CH)

(72) Inventors: Denis Shcherbakov, Plainsboro, NJ (US); Addi Fadel, Plainsboro, NJ (US); Nicholas O'Leary, Plainsboro, NJ (US)

(73) Assignee: Firmenich SA, Satigny (CH)

(*) Notice: Subject to any disclaimer, the term of this patent is extended or adjusted under 35 U.S.C. 154(b) by 534 days.

(21) Appl. No.: 18/003,149

(22) PCT Filed: Sep. 30, 2021

(86) PCT No.: PCT/EP2021/076950
§ 371 (c)(1),
(2) Date: Dec. 22, 2022

(87) PCT Pub. No.: WO2022/069634
PCT Pub. Date: Apr. 7, 2022

(65) Prior Publication Data
US 2023/0253075 A1 Aug. 10, 2023

Related U.S. Application Data

(60) Provisional application No. 63/175,635, filed on Apr. 16, 2021, provisional application No. 63/134,449,
(Continued)

(30) Foreign Application Priority Data

Nov. 17, 2020 (EP) .................................... 20208016

(51) Int. Cl.
*G16C 20/30* (2019.01)
*B01L 5/02* (2006.01)
*G16C 60/00* (2019.01)

(52) U.S. Cl.
CPC ................ *G16C 20/30* (2019.02); *B01L 5/02* (2013.01); *G16C 60/00* (2019.02)

(58) Field of Classification Search
CPC ............ G16C 20/30; G16C 60/00; B01L 5/02
See application file for complete search history.

(56) References Cited

U.S. PATENT DOCUMENTS

2003/0172717 A1* 9/2003 Kita .................. G01N 33/0031 73/23.34
2018/0188224 A1* 7/2018 De Oliveira ............. A61B 5/16

FOREIGN PATENT DOCUMENTS

EP 2 502 978 A1 9/2012
EP 2502978 * 9/2012 ............... C11B 9/00
(Continued)

OTHER PUBLICATIONS

Hideiki Wakayama et al., "Method for Predicting Odor Intensity of Perfumery Raw Materials Using Dose-Response Curve Database", : Ind. Eng. Chem. Res. 2019, 58, pp. 15036-15044.*
(Continued)

*Primary Examiner* — Alexander Satanovsky
(74) *Attorney, Agent, or Firm* — Knobbe, Martens, Olson & Bear, LLP

(57) ABSTRACT

The fragrance ingredient or composition spatial recognisability prediction method (200) to prepare a fragrance composition comprising said fragrance ingredient or composition, comprises the steps of: —selecting (205), upon a computer interface, a value representative of between one and two of the following parameters: —a minimum sensory intensity level, corresponding to a predetermined minimum
(Continued)

psychophysical intensity for the ingredient, —a maximum distance, corresponding to a distance at which the ingredient is to be perceived at a minimum predetermined psychophysical intensity level or—a quantity of the ingredient in liquid phase, wherein the selected value is selected within a range of at least two distinct values, —computing (215), by a computing system, a value representative of either one of the following parameters: —a minimum sensory intensity level, corresponding to a predetermined minimum psychophysical intensity for the ingredient, —a maximum distance, corresponding to a distance at which the ingredient is to be perceived at a minimum sensory intensity level selected or set by default, or—a quantity of the ingredient in liquid phase and wherein the computed value is representative of a parameter other than the parameter associated with the selected value and wherein a value for the parameter neither selected nor computed is set to a default value, said ingredient digital identifier corresponding to a physical ingredient to be used within a fragrance composition to be prepared as a function of the computed and selected values.

13 Claims, 11 Drawing Sheets

Related U.S. Application Data filed on Jan. 6, 2021, provisional application No. 63/085,183, filed on Sep. 30, 2020.

(56) References Cited

FOREIGN PATENT DOCUMENTS

| | | | |
|---|---|---|---|
| WO | 2015/181257 | A2 | 3/2015 |
| WO | 2019/122306 | A1 | 6/2019 |
| WO | 2019/238680 | A1 | 12/2019 |

OTHER PUBLICATIONS

Joana Pereira et al., "Modelling Diffusion of Fragrances: a Radial Perspective", The Canadian Journal of Chemical Engineering, , vol. 97, Jan. 2019, pp. 351-360.*

Edge B.A. et al. "Computational study of the wake and contaminant transport of a walking human", J. Fluids Eng., vol. 127, pp. 967-977 (Sep. 2005).

Incorvia M. et al. "Improving Fragrance Performance Using Intensity Plots", Perfumer & Flavorist, vol. 27, pp. 38-43 (Mar./Apr. 2002).

Mookherjee B. et al. "Fragrance emission from the skin", Cosmetics & Toiletries, vol. 113, No. 7, pp. 53-56 and 58-60 (Jul. 1998), 113(7).

Neuner-Jehle N. et al. "The Measuring of Odors", Perfumes Art, Science & Technol, eds. Müller P.M. et al., chapter 6, pp. 153-212 (1991).

Periera J. et al. "The Trail of Perfumes", Am Inst Chem Eng J, vol. 64, No. 7, pp. 2890-2897 (Jul. 2018).

Pereira J. et al. "Modelling diffusion of fragrances : A radial perspective", Canadian Journal of Chemical Engineering, vol. 97, No. 1, pp. 351-360 (Jul. 16, 2018).

Teixeira M.A. et al. "The Perception of Fragrance Mixtures: A Comparison of Odor Intensity Models", Am Inst Chem Eng J, vol. 56, No. 4, pp. 1090-1106 (Apr. 2010).

Vuilleumier C. et al. "Multidimensional Visualization of Physical and Perceptual Data Leading to a Creative Approach in Fragrance Development", Perfumer & Flavorist, vol. 33, pp. 54-61 (Sep. 2008).

Wakayama H. et al. "Method for Predicting Odor Intensity of Perfumery Raw Materials Using Dose-Response Curve Database", Industrial & Engineering Chemistry Research, vol. 58, No. 32, pp. 15036-15044 (Jul. 19, 2019).

Zhang L. et al. "A machine learning based computer-aided molecular design/screening methodology for fragrance molecules", Computers & Chemical Engineering, vol. 115, pp. 295-308 (Apr. 25, 2018).

* cited by examiner

FRAGRANCE INGREDIENT SPATIAL RECOGNISABILITY PREDICTION METHODS AND FRAGRANCE COMPOSITION SPATIAL RECOGNISABILITY PREDICTION METHODS

This present application is a U.S. national phase entry under 35 U.S.C. § 371 of PCT Application No. PCT/EP2021/076950, filed Sep. 30, 2021, which claims priority to U.S. Provisional Application No. 63/085,183, filed Sep. 30, 2020, European Patent Application No. 20208016.4, filed Nov. 17, 2020, U.S. Provisional Application No. 63/134,449, filed Jan. 6, 2021, and U.S. Provisional Application No. 63/175,635, filed Apr. 16, 2021. The entire contents of these applications are explicitly incorporated herein by this reference.

TECHNICAL FIELD OF THE INVENTION

The present invention relates to fragrance ingredient spatial recognisability prediction methods and fragrance composition spatial recognisability prediction methods. It applies, in particular, to the field of perfumery. More precisely, the invention can apply to the fields of fragrance performance modelling and visualisation, of digital tools for intelligent design of fragrance compositions, of performance optimisation of fragrance compositions, of spatial and temporal performance attributes of fragrances, and more specifically trail performance of fine fragrances.

BACKGROUND OF THE INVENTION

Fragrance performance, particularly in the context of fine fragrances, can be divided into three main attributes: impact, long-lastingness, and projection, the latter comprised of 'diffusion' and trail characteristics. Projection (sometimes also referred to as 'volume' in the art) describes how well the fragrance can be perceived at a distance by other people.

The term 'diffusion' in the field of perfumery generally means how effectively the fragrance (or a fragrant ingredient) can be perceived in the 'aura', or, the immediate vicinity, of the fragrance source (the fragrance wearer). The aura, in this context, is defined by the space around the source of a fragrance, where diffusion from the vapour-liquid interface (i.e., liquid perfume on skin exposed to air) is a relevant transport mechanism. Such a definition is also present in the following publication: 'A Novel Technology to Study the Emission of Fragrance from the Skin', by Braja D. Mookherjee, Subha M. Patel, Robert W. Trenkle and Richard A. Wilson in Cosmetics & Toiletries (1998), 113(7), 53-56, 58-60. This term should be opposed to the 'trail', or 'sillage', in which the main transport vector is overwhelmingly convection resulting from movement of the fragrance source or the airflow or both.

Indeed, most common circumstances of fragrance wear involve some type of ventilation or airflow (convection) whether the fragrance wearer is sitting in an office or walking. The air flow can be induced by various means, such building ventilation, active movement of the wearer, recent movement of the wearer, wind, or natural convection due to body heat. The intensity of air convection around the wearer is what sets apart different circumstances of fragrance wear, each relating to different extents of gas-phase dilution of the fragrance plume in surrounding air as the fragrance travels (projects) from the wearer.

The fragrance trail phenomenon is associated with substantial, in fact, turbulent, convective airflow around the fragrance wearer, which can be caused by either the motion of the person (walking) or the motion of the surrounding air (wind), or both. Performance of a fragrance in the trail can therefore be thought of as the ultimate stress test for fragrance performance; in other words, gas-phase dilution by the surrounding air of the fragrance emanating from the wearer is the most extensive in the case of trail compared to all the other circumstances of fragrance wear.

Although fragrance trail is often referenced in both patent literature and scientific publications, a gap in the published art still exists in terms of realistic quantitative data or predictions on gas-phase fragrance dilution around a walking person and applying such data to benefit fragrance performance at a distance and practical fragrance optimisation for trail performance based on that knowledge together with the knowledge of human olfactive dose-response characteristics of fragrance ingredients.

The absence of any of the knowledge blocks mentioned in the previous paragraph makes it impossible to predict, or estimate, with any reliability the spatial recognisability of a mixture of ingredients, making it necessary to resort to the time-consuming, laborious process of empirically assembling said mixture and measuring said recognisability via sensory panels. Such constraints considerably slow down the fragrance (mixture) design process, drive up the cost of fragrance development process, and are wasteful of valuable raw materials.

For example, current systems and methodologies used on the website fragrantica.com provide for a multitude of fragrance products empirical classifications for trail performance of fragrances in terms of distance from the wearer to which the fragrance projects. However, the data on such classifications are derived from informal consumer polls conducted by the website, and although such empirical classifications could be used to rank fragrances by performance, fragrance creation rules that would lead to superior trail performance cannot be gathered from such data alone.

Other current systems and methodologies approach performance of a fragrance by the Odor Value of its constituent ingredients. Odor Value of a perfumery ingredient is the ratio of the equilibrium gas-phase concentration, also known as saturation concentration, for said ingredient (commonly referred to as 'volatility') to the gas-phase concentration for said ingredient at its odour detection threshold. The terms Odor Value and Odor Detection Threshold are well known to a person skilled in the art of perfumery, human sensory perception, or a related field, and are used extensively in the prior art.

The deficiency of Odor Value as a metric for trail performance of fragrances and other aspects of fragrance performance is two-fold.

First, since the Odor Value concept is based on the odour detection threshold, any ingredient performance metric based on the Odor Value requires only that the ingredient must be present in the gas phase at its odour detection threshold, meaning that it has to be merely detectable to a human nose. This criterion is necessary but not sufficient for setting performance targets for ingredients and fragrances in perfumery applications, where customers expect the scent and its ingredients to be perceived at such a finite intensity that an ingredient or a fragrance can be recognised and interpreted, rather than merely detected. Since Odor Value is based on the minimum possible sensory perception signal for any ingredient, which is detection, Odor Value-based performance metrics systematically overstate performance capacity of fragrance ingredients, both on their own and in fragrance compositions. Sensory detection as a criterion for performance and the Odor Value as a performance metric are therefore impractical and insufficient for performance-driven fragrance design and optimisation where realistic, quantitative predictions are needed.

Second, when comparing performance of different ingredients, performance metrics based on Odor Value—the latter in turn linked to odour detection—are not predictive of relative ingredient performance at higher perceived intensities, such as those linked to odour recognition, relevant to realistic perfumery product applications.

FIG. 1 shows the psychophysical intensity 140 of a fragrant ingredient as a function of the gas phase concentration 135 of said ingredient. Such a function is called a 'dose-response curve', which in the case of FIG. 1 is represented for both alpha damascone 115 and delta damascone 120.

The lowest gas phase concentration at which the ingredient is perceived (detected by a human nose) is called the Odor Detection Threshold, 105 and 110. In the Odor Value performance estimation paradigm, the Odor Value quantifies in terms of a mathematical ratio the difference between the maximum gas phase concentration at equilibrium conditions and the minimum gas phase concentration allowing human olfactory detection of the compound. Odor Detection Threshold is measured by a series of triangle tests, where sensory results are expressed as percentages of correct answers from randomised sensory tests which include both odourless blanks and actual fragrant raw material. Odor detection threshold typically corresponds to 50% of correct answers from a sensory panel; however, for triangle tests, a criterion of 67% correct answers is used.

Delta damascone has a higher Odor Value than alpha damascone, which would imply in the Odor Value-based performance estimation paradigm that delta damascone is a higher-performing ingredient and has a larger dilution range than alpha damascone, based on the sensory criterion of odour detection. However, at higher sensory intensities, the dose-response curves of these two ingredients cross over twice, with alpha damascone maintaining a higher performance compared to delta damascone.

A relevant discourse on the Odor Value and its deficiencies are provided, for example, in N. Neuner-Jehle, F. Etzweiler. 'The Measuring of Odours'. In Perfumes: Art, Science & Technology. P. M. Müller, D. Lamparsky, eds. Chapter 6, p. 153. Elsevier Applied Science: 1991. In this publication, perfume performance is discussed in the context of the odour value. Odor detection thresholds of ingredients are introduced as per the Stevens' psychophysical power function applied to the odour intensity-concentration relation. The odour value concept is simply introduced as defined as the quotient of ingredient saturation concentration in the gas phase (at equilibrium) and ingredient odour detection threshold concentration in the gas phase, both usually given in the units of nanograms per litre of air.

The authors specifically mention that the odour value can be a relative and approximative measure for odour intensity but has limitations. The limitations include:

- perfume intensity does not increase linearly with fragrance concentration based on the psychophysical power law function; in other words, concentration ratios from which odour values are derived cannot be a numerical equivalent for odour intensities beyond odour detection and
- the odour intensity of different odorants increases with concentration at different rates, where two odorants can be perceived with very different odour intensities even though they may be used in a composition at a level at which their partial odour values in composition (i.e. based on partial volatilities, taking into account mixture composition) are identical.

The approach utilising classical Odor Value can be seen in the international patent application WO 2019/122306, filed by Givaudan and titled 'Method and apparatus for creating an organic composition'. This publication discloses a fragrance/flavour design system: a computer terminal arranged to allow a user to produce a fragrance or flavour composition, the terminal comprising a processor, a database connection to a database storing ingredients, an output connection to an output device configured to produce a sample of the composition, a display and a user input means; wherein the processor is configured to: accept selection via the user input means of ingredients from the database; add pictograms representing the selected ingredients to an olfactive design space on the display, wherein the size of the pictogram for each selected ingredient represents that selected ingredient's olfactive contribution to the composition; convert for each selected ingredient, its olfactive contribution to a corresponding quantity of the ingredient; and, when the user requests a sample of the composition via the input means, to instruct the output device to dispense the corresponding quantity of the selected ingredients.

Although this publication focuses predominantly on the design of visual fragrance creation portal, connected to various databases and peripheral devices, this publication does reference certain elements that relate to how ingredient performance metrics in compositions are approached and evaluated:

- the Odor Value concept is referenced extensively with detailed specifications as the preferred measure of ingredient performance, both in and outside of compositions;
- the publication mentions the dose-response curves as an additional possible attribute of performance: 'Additionally, dose-response curves may be stored (locally or remotely) and visualised, providing additional impact score. Dose-response curves express the evolution of the impact of an ingredient as a function of the concentration of this ingredient in the headspace', although without specifying any details on how such dose-response data would be translated to a quantitative metric for guiding formulation (dosages in composition) or prediction of performance at a distance; and
- the publication mentions 'hydrodynamic transport equations for both diffusion and convection regimes' as an example of a suitable approach that may be implemented in the portal to calculate attributes such as trail: 'Spatio-temporal performance criteria, such as tenacity, substantivity, bloom, radiance, volume, and trail, may also be incorporated as useful attributes. Optionally, these attributes may be calculated by using suitable algorithms implemented in the creation tool. Examples of suitable algorithms include Vapour Liquid Equilibrium (VLE) calculation and the calculation of the hydrodynamic transport equations for both diffusion and convection regimes'. However, while vapour-equilibrium calculations are straightforward to the person skilled in the art, hydrodynamic transport equations for diffusion and convection can be approached through a multitude of geometries and calculation methods, and implications of such calculations on fragrance performance prediction is not specified in any detail.

Similar approach based on Odor Value can be seen, as well, in the international patent application WO 2015/181257, filed by Givaudan and titled 'Perfume compositions'. This publication discloses perfume compositions claimed to exhibit controlled or desirable spatiotemporal olfactory profiles. The disclosure also relates to a method of quantifying said spatiotemporal olfactory profiles of said compositions. This publication mentions and discusses trail (sillage) performance of fragrances, again in the framework of the Odor Value as a performance metric, as well as a device constructed to assess trail (sillage) performance sensorially. The intent of this prior art appears to be two-fold: (1) to formulate fragrance compositions claimed to exhibit strong trail performance based on the knowledge of Odor Value of the constituent ingredients, which relies on the knowledge of ingredient volatility and odour detection threshold, by selecting high-performance ingredients through a graphical approach leveraging Odor Value (log-log plots and lines delineating certain performance zones); (2) to provide a device and a measurement method for assessing trail of fragrances. The authors claim high-performance fragrance ingredients (including for trail) based on volatility and odour detection thresholds.

This publication suffers from the same deficiencies as the previously mentioned disclosures, including the usage of the classical Odor Value as the metric for ingredient selection and performance for various modes of fragrance wear and usage including trail.

Therefore, as it can be understood, since all known fragrance performance prediction methods known in the prior art employ the Odor Value concept that is based on the odour detection threshold, there exists no method to predict, or simulate, for actual circumstances of fragrance trail the performance of a fragrance and its constituent ingredients at a distance that is based on actual fragrance wear and usage habits of consumers.

SUMMARY OF THE INVENTION

The present invention is intended to remedy all, or part of the disadvantages associated with the prior art.

The inventors have discovered a novel way of linking the quantity and the composition of a fragrance applied on a wearer to spatial reach of the ingredient at requested perceived intensity level in the trail behind the wearer, so that it can be perceived by the receptor of the scent at a specific distance and at a specified minimum sensory intensity level.

In particular, regarding FIG. 1 as an example, if a different target intensity 145 criterion is chosen as the basis for the ingredient performance metric, instead of the odour detection threshold, superior performance of alpha damascone over delta damascone can be quantitatively captured in the practical range of perceived intensities linked to consumer fragrance products and consumer usage.

The application of this discovered novel relationship allows for the prediction of the performance of a fragrance based on fragrance wear and usage habits of consumers in a variety of scenarios:

- predicting the distance from the source (wearer) at which the fragrance (and/or its constituents) can be perceived at a target intensity as a function of quantity and composition of the fragrance on skin (liquid phase),
- predicting the distance from the source (wearer) at which the fragrance (and/or its constituents) can be perceived for a target quantity as a function of intensity and composition of the fragrance on skin (liquid phase),
- predicting the quantity and composition of the fragrance on skin (liquid phase) needed to reach a predetermined distance for a target perceived intensity,
- predicting the quantity and composition of a fragrance on skin (liquid phase) needed to reach a target distance for a minimum predetermined perceived intensity,
- predicting the perceived intensity of a fragrance and its constituent ingredients for a predetermined distance and a target quantity in liquid phase and/or
- predicting the perceived intensity of a fragrance and its constituent ingredients for a target distance and a predetermined quantity in liquid phase.

In the context of this invention, 'trail' is defined as opposed to 'aura', both combining aspects of time and distance. Aura of the fragrance forms in the immediate vicinity of the wearer, and it is synonymous with minor, if any, movement of the wearer or air agitation. Aura is essentially the first emission of the fragrance from the skin or clothes and into the gas phase and its first transmission into the immediate vicinity of the wearer, which then feeds the trail when movement of the wearer and/or additional air convection is/are incorporated. Trail is synonymous with movement of the wearer such as walking or air movement such as wind, or both together. Trail is evaluated by other people and should be perceived at desired sensory intensity (such as, for example, intensity linked to odour recognition) at distances of at least 1 metre away, preferably 2 metres away, and most preferably 4 metres away, after the fragrance has settled into a 'dry-down' phase at least 30 minutes from application, preferably after at least 1 hour from application, more preferably after at least 2 hours, and most preferably after at least 4 hours from application.

It should be noted here that volatility itself is a gas-phase saturation concentration and is a derived rather than a fundamental property, which can be either measured or calculated from the vapour pressures and can also be related to boiling points (for liquids) in a similar way that vapour pressures relate to boiling points. High vapour pressures indicate a high volatility, while high-boiling points indicate low volatility. Vapour pressures and boiling points are often presented in property tables and charts that can be used to compare chemicals of interest.

In the context of this invention, volatility is preferably expressed in units of concentration such as micrograms of compound per litre of air and corresponds to the maximum concentration that an ingredient in its gaseous state can achieve at equilibrium at a given temperature with its liquid or solid phase in a closed system.

Volatility is relevant not only for describing the process of evaporation but also as a scale for odour performance, or olfactive performance, of an ingredient when a gas phase concentration associated with its desired perception level or human olfactory response is known. Said gas phase concentration can define either the Odor Detection Threshold—a gas phase concentration at which an odour can be detected—or, as can be used within the scope of the current invention, a specific finite perceived intensity that is part of an ingredient's dose-response curve and that could include perceived intensity linked to sensory recognition threshold—a gas phase concentration at which an odour can be correctly identified and/or described.

In the context of this invention, an ingredient designated a 'volatile ingredient' presents a vapour pressure of at least 1E-6 mm Hg (0.000001 mm Hg) at ordinary room temperature of 22 C. Such an ingredient evaporates non-negligibly at temperatures above a minimal temperature threshold representative of a minimal temperature intended for the use of the compound. For example, if an ingredient is intended to be used in a fragrance that should be perceived in everyday life, that minimal temperature might be 0° C. In this example, at temperatures above 0° C., the ingredient forms a fragrant vapour called 'gas phase' that can be perceived by a human nose. Such a chemical ingredient can also be defined by the molecular mass of said ingredient. According to this method of definition, a volatile ingredient is an ingredient presenting a molecular mass below 350 Da. Preferably, a volatile ingredient is an ingredient presenting a molecular mass below 325 Da. Preferably, a volatile ingredient is an ingredient presenting a molecular mass below 300 Da.

It should be noted that the terms 'upon a computer interface' are generally defined by the action of inputting an instruction to a computing system.

Such input action may use a human-machine interface, such as a keyboard, a mouse, a touchscreen or any interactive GUI (for 'Graphical User Interface') accepting an input from a user.

In variants, the input considered is a logic input, such as a command received via an information technology network (wireless or not) by the computing system, the interface, in this scenario, being the logical 'port' of a software running upon the computing system.

The input considered may be the result of a human decision or be automatically determined by a computing system.

It should be noted that the terms 'computing system' designate any electronic calculation device, whether unitary or distributed, capable of receiving numerical inputs and providing numerical outputs by and to any sort of interface, digital and/or analog. Typically, a computing system designates either a computer executing a software having access to data storage or a client-server architecture wherein the data and/or calculation is performed at the server side while the client side acts as an interface.

It should be understood here that the inventors have found a novel way of characterising and utilising, for the purposes of performance improvement of a fragranced consumer product, the dilution of an ingredient in the wake of a walking human (or, equivalently, stationary human in the path of an air current, such as wind) that creates fragrance trail, as a function of distance between the position of the ingredient at the source (fragrance wearer) and the position of a sensor (such as a human nose) for that ingredient. Such a relationship has not been used before in a reliable, quantitative, and realistic way as it relates to the context of fragrance wear by consumers.

The term 'recognisability' is defined by the likelihood, for a plurality of persons smelling a fragrance, to perceive, and more preferably recognise or correctly describe, the olfactory character of an ingredient in the gas phase at a specified distance from the fragrance source (the wearer). Recognisability and detectability are two distinct concepts, in that the latter is concerned with the likelihood, for a plurality of persons smelling a fragrance, to detect the presence of an odour without being able to recognise or correctly describe the odour character associated to this ingredient or, more preferably, the ingredient itself.

The term 'distance' refers to the spatial distance between two objects, such as a perfume wearer and a person in contact with the gas phase of said perfume located within a distance and the direction corresponding, for example, to the fragrance trail.

The term 'sensory intensity level' refers to a value of perceived psychophysical intensity for an ingredient, specified from within the range defined by the dose-response relationship for said ingredient. Sensory intensity levels can be expressed in absolute terms, such as for example 3.5 on a 10-point scale, or as a percentage of the scale maximum, such as for example 35% of the scale. Absolute and relative definitions are interchangeable and can be easily interconverted if the maximum of a desired scale to be used is specified.

The term 'fragrance source' refers to a geographical location at which a fragrance ingredient or composition is located in liquid form, either in bulk or dispersed upon a surface.

The term 'maximum total dilution' refers to fragrance ingredient dilution that includes both its liquid-phase dilution in a fragrance composition (mixture), such as measured by its weight fraction in a fragrance composition, and its spatial dilution by air in the gas phase at a specified distance given relative to its gas-phase concentration at the liquid air (vapour liquid) interface. The term 'maximum total dilution' includes the word 'maximum' because it is specified to satisfy a sensory criterion of at least a selected minimum perceived intensity of an odorous ingredient.

The term 'relative ingredient quantity' or 'relative quantity' refers to the weight fraction of an ingredient in a given fragrance composition, or fragrance formula, including multiple ingredients, solvents, and/or other functional raw materials.

The term 'ingredient quantity' or 'composition quantity' refers to the absolute amount (mass or volume) of fragrance applied onto the human body in liquid or solid form by a consumer, such as by a fragrance spray. Where ingredient quantity or composition quantity are not explicitly specified, a default value is always used unless explicitly changed by the user. Pre-computed functional relationships between spatial dilution and downstream distance from the fragrance wearer are retrieved based on information provided about air flow velocities, part(s) of the body where the fragrance is applied, and the quantity of fragrance or ingredient applied, the latter translated to a surface area on the body comprising the fragrance source.

Fragrance wear and usage habits of consumers can be defined in technical terms for the consumer product application of interest, and such technical definition is required for development of a robust technical prediction method such as described in this invention. For example, for fine fragrances, the technical specifications for the prediction method may include, but are not restricted to,

- 5-20% fragrance application in a hydroethanolic mixture;
- 2-4 sprays of fragrance applied by the consumer on various areas of the body, which may include neck, chest, shoulders, arms, or various pulse points and which may cover a surface area on the body between 50 and 500 $cm^2$;
- an average walking speed of 1.0 to 1.4 m/s;
- a distance from the wearer along the downstream direction of the airflow, which ranges from close to skin to beyond 4 metres;
- desired sensory intensity of constituent ingredients in a fragrance at a given distance, which is normally chosen from but not limited to the lower half of the sensory perception scale (i.e. up to 5 on a 10-point scale); and
- time from application on skin at which desired sensory intensity level should be achieved.

Sensory intensity level is a well-defined quantity that is either measured on a predetermined scale from statistically treated responses of a plurality of human panellists or estimated from mathematical expressions describing available human olfactory dose-response relationships, the latter also constructed from statistically treated responses of preferably 30 or more human panellists. Preferred sensory intensity levels describing fragrance performance differ across consumer product applications as well as geographic regions, where consumers may prefer a certain facet of fragrance performance to be more or less pronounced. Preferred sensory intensity levels are determined rigorously from human sensory panels, employing a plurality of subjects and results of such panels statistically treated, and fed as parameters to the fragrance performance prediction model of the current invention.

Preferred sensory intensity level of a fragrance ingredient or a fragrance composition can, for example, be associated with the recognition threshold of such ingredient or composition determined from results of a human sensory panel. Recognition threshold is a sensory intensity or, equivalently, a gas phase concentration at which a fragrance ingredient or a fragrance composition can be recognised and correctly identified or described by a human sensor.

One key differentiating feature of the present invention over the prior art is the incorporation of predetermined sensory intensity levels in real conditions of fragrance use as parameters in the performance prediction method, which allows realistic estimation of performance of fragrance ingredients in a given composition as well as estimation of their preferred usage levels in fragrance compositions such as to achieve desirable sensory performance. Any prediction method or approach involving Odor Value does not have the capability to specify a predetermined sensory intensity criterion for fragrance performance because Odor Value, by definition, is tied to the odour detection threshold only, instead of any range of sensory intensity levels that can be specified in the current invention.

According to a first aspect, the present invention aims at a fragrance ingredient or composition spatial recognisability prediction method to prepare a fragrance composition comprising said fragrance ingredient or composition, comprising the steps of:

- selecting, upon a computer interface, a value representative of between one and two of the following parameters:
  - a minimum sensory intensity level, corresponding to a predetermined minimum psychophysical (or sensory) intensity for the ingredient,
  - a maximum distance, corresponding to a distance at which the ingredient is to be perceived at a minimum predetermined psychophysical intensity level, or
  - a quantity of the ingredient in liquid phase,
- wherein the selected value is selected within a range of at least two distinct values,
- computing, by a computing system, a value representative of either one of the following parameters:
  - a minimum sensory intensity level, corresponding to a predetermined minimum psychophysical intensity for the ingredient,
  - a maximum distance, corresponding to a distance at which the ingredient is to be perceived at a minimum sensory intensity level selected or set by default, or
  - a quantity of the ingredient in liquid phase and
- wherein the computed value is representative of a parameter other than the parameter associated with the selected value and wherein a value for the parameter neither selected nor computed is set to a default value, said ingredient digital identifier corresponding to a physical ingredient to be used within a fragrance composition to be prepared as a function of the computed and selected values.

Such provisions provide similar advantages to the sum of all other aspects of the present invention.

According to a second aspect, the present invention aims at a fragrance ingredient or composition spatial recognisability prediction method to prepare a fragrance composition comprising said fragrance ingredient or composition, comprising the steps of:

- selecting, upon a computer interface, a value representative of a minimum requested sensory intensity level, corresponding to a desirable predetermined perceived minimum psychophysical intensity for the ingredient, said value being selected within a range of at least two distinct values,
- determining, by a computing system, a value representative of a minimum gas phase concentration of the ingredient corresponding to the selected minimum sensory intensity level as a function of a dose-response curve linking gas phase concentration to the selected minimum sensory intensity,
- calculating, by a computing system, a maximum total acceptable ingredient dilution, for both in gas and liquid phases of the fragrance, as a function of the determined minimum gas phase concentration and
- computing, by a computing system, at least one value representative of a distance from the fragrance source, up to a maximum distance from the fragrance source, at which the ingredient presents at least the minimum sensory intensity level selected as a function of the maximum total ingredient dilution calculated, said computing step comprising a step of retrieving, from an electronic storage, at least one value representative of the minimum spatial dilution for an ingredient in the gas phase corresponding to a predetermined downstream distance from the fragrance source.

Such provisions allow for the accurate prediction and optimisation of fragrance performance at distances representative of fragrance trail. Indeed, the use of a variable minimum sensory intensity level allows for the definition of a minimum performance threshold for each ingredient in a fragrance, said threshold allowing for the calculation of a maximum distance at which a fragrance ingredient can deliver requested sensory performance, such as a specific perceived intensity. Such a relationship between performance threshold and distance allow for a realistic, quantitative and reliable performance prediction and assessment for fragrance ingredients and for complete fragrance compositions. Such knowledge allows for the advanced design of multi-ingredient fragrances, for example, with specific performance requirements in terms of distance and time.

In particular embodiments, the step of computing comprises a step of retrieving, from an electronic storage, at least one value representative of the minimum spatial dilution for an ingredient in the gas phase corresponding to a predetermined downstream distance from the fragrance source, said value being used to compute the maximum downstream distance from the fragrance source at which the ingredient presents at least the minimum sensory intensity level selected.

Such embodiments allow for the use of precalculated gas-phase dilution levels, based upon dilution calculation algorithms, such as computational fluid dynamics for instance, in the determination of the distance associated to the fragrance ingredient or composition performance level selected, such as the minimum sensory intensity.

In particular embodiments, the method object of the present invention comprises, prior to the step of retrieving, a step of constructing a minimum spatial dilution electronic storage, said step of constructing matching minimum spatial dilution values to at least one distance from a fragrance source value and at least one of the following indicators:

an indicator representative of an incoming air flow velocity incident upon the fragrance source comprising said ingredient, an indicator representative of an ingredient or fragrance composition application surface area, an indicator representative of simulation parameters for the shape of a human body and/or an indicator representative of area location on a human body upon which the ingredient or fragrance composition is applied, said step of constructing comprising a step of computational fluid dynamics simulation configured to calculate said spatial dilution values at predetermined downstream distances from the source.

Such embodiments allow for the use of advanced computational fluid dynamics calculation algorithms which, in turn, allow for the accurate prediction of gas-phase concentrations of fragrance ingredients at a given distance from the fragrance wearer, which are in turn converted to dimensionless spatial dilutions, or spatial dilution factors, and linked to ingredient performance metrics for fragrance composition design.

In particular embodiments, the method object of the present invention comprises a step of setting a value representative of a duration of dry down of an ingredient, the step of computing of a value representative of a distance from the fragrance source being achieved as a function of the duration of dry down set.

Such embodiments allow for the spatiotemporal analysis of the performance of all ingredients in a fragrance composition at distances representative of fragrance trail.

According to a third aspect, the present invention aims at a fragrance ingredient spatial recognisability prediction method to prepare a fragrance composition comprising said fragrance ingredient or composition, comprising the steps of:

selecting, upon a computer interface, a value representative of a distance within a range of at least two distinct values and up to a maximum downstream distance from the fragrance source at which the ingredient presents a minimum sensory intensity level corresponding to a predetermined minimum psychophysical intensity for the ingredient, retrieving, from an electronic storage, a minimum spatial dilution value associated with the selected distance, determining, by a computing system, a value representative of gas phase concentration of the ingredient corresponding to the spatial dilution value retrieved and computing, by a computing system, for the selected value of distance, at least one value representative of a sensory intensity level as a function of a dose-response curve linking gas phase concentration to sensory intensity level.

Such provisions provide similar advantages to the second aspect of the present invention but provide the inverse of the first aspect, where instead of calculating a distance linked to a requested perceived intensity, a sensory intensity is calculated at a distance of interest.

According to a fourth aspect, the present invention aims at a fragrance ingredient or composition spatial recognisability prediction method to prepare a fragrance composition comprising said fragrance ingredient or composition, comprising the steps of:

selecting, upon a computer interface, a value representative of a minimum sensory intensity level to be achieved, corresponding to a predetermined minimum psychophysical intensity for the ingredient, selecting, upon a computer interface, a value representative of a downstream distance from a fragrance source, determining, by a computing system, a value representative of the gas phase concentration of the ingredient corresponding to the selected minimum sensory intensity level as a function of a dose response for said ingredient linking gas phase concentration to the selected minimum sensory intensity, retrieving, from an electronic storage, a value of minimum spatial dilution as a function of the selected distance from the fragrance source, calculating, by a computing system, at least one value representative of maximum total ingredient dilution as a function of the determined gas phase concentration for said ingredient and computing, by a computing system, for at least one value representative of maximum total ingredient dilution calculated and at least one value representative of minimum spatial dilution retrieved for the selected distance, at least one value representative of a quantity of ingredient in liquid phase, so that the ingredient presents the minimum sensory intensity level as a function of the value of ingredient dilution at the predetermined distance.

Such provisions provide similar advantages to the second aspect of the present invention but additionally also allow explicit prediction of ingredient usage levels in composition to provide the level of performance specified by a minimum sensory intensity and a minimum distance from the wearer at which this intensity is perceived.

According to a fifth aspect, the present invention aims at a fragrance composition spatial recognisability prediction method to prepare a fragrance composition comprising said fragrance ingredient or composition, comprising the steps of:

electing, upon a computer interface, at least two ingredient digital identifiers to form a fragrance source, setting, upon a computer interface, a value representative of a relative quantity of at least one said ingredient identified by said digital identifier, selecting, upon a computer interface, a value representative of a minimum requested sensory intensity level, corresponding to a desirable predetermined perceived minimum psychophysical intensity for at least one ingredient, said value being selected within a range of at least two distinct values, determining, by a computing system, a value representative of a minimum gas phase concentration for each said ingredient corresponding to the selected minimum sensory intensity level as a function of a dose-response curve linking gas phase concentration to the selected minimum sensory intensity, calculating, by a computing system, a maximum total ingredient dilution, for both in gas and liquid phases of the fragrance, as a function of the determined minimum gas phase concentration, for each said ingredient and computing, by a computing system, at least one value representative of a distance from the fragrance source, up to a maximum distance from the fragrance source, at which at least one ingredient presents at least the minimum sensory intensity level selected as a function of the maximum total ingredient dilution calculated.

Such provisions provide similar advantages to the second aspect of the present invention for multi-ingredient fragrances.

In particular embodiments, at least one ingredient digital identifier is associated, in a computer memory, to a descriptor representative of the scent of the corresponding ingredient, wherein the method further comprises a step of providing, upon a computer interface, at least one alternative ingredient digital identifier to at least one of the elected ingredient digital identifiers as a function of at least one descriptor associated to said elected ingredient digital identifier.

Such embodiments allow for advanced fragrance design capabilities, providing intelligent insights to perfumers and other users of the interface skilled in the art of perfumery.

In examples of such embodiments, if one ingredient is associated to a given descriptor, said ingredient may be a candidate for replacement by another ingredient associated to the same descriptor if the latter ingredient can achieve a better maximum spatial reach or perceived intensity compared to the ingredient under original consideration.

In particular embodiments, the step of providing is achieved as a function of both at least one descriptor associated to said elected ingredient digital identifier and the computed value representative of a maximum downstream spatial distance for said ingredient digital identifier.

Such embodiments allow for advanced fragrance design capabilities, providing intelligent insights to perfume designers.

According to a sixth aspect, the present invention aims at a fragrance composition spatial recognisability prediction method to prepare a fragrance composition comprising said fragrance ingredient or composition, comprising the steps of:

- electing, upon a computer interface, at least two ingredient digital identifiers forming a fragrance source,
- setting, upon a computer interface, a value representative of a relative quantity of at least one said ingredient identified by said digital identifier,
- selecting, upon a computer interface, a value representative of a distance within a range of at least two distinct values and up to a maximum downstream distance from the fragrance source at which at least one ingredient presents a minimum sensory intensity level corresponding to a predetermined minimum psychophysical intensity for each said ingredient,
- retrieving, from an electronic storage, a minimum spatial dilution value associated with the selected distance,
- determining, by a computing system, a value representative of gas phase concentration of at least one said ingredient corresponding to the spatial dilution value retrieved and
- computing, by a computing system, for the selected value of distance, at least one value representative of a sensory intensity level as a function of a dose-response curve linking gas phase concentration to sensory intensity level.

Such provisions provide similar advantages to the fifth aspect of the present invention.

According to a seventh aspect, the present invention aims at a fragrance composition preparation method, comprising:

- a step of selecting, upon a computer interface, at least one ingredient digital identifier to form a fragrance composition digital representation,
- a step of predicting, by a computing device, a spatial recognisability for at least one selected ingredient digital identifier according to a fragrance composition spatial recognisability prediction method according to any one of claims 1 to 10 and
- a step of preparing a fragrance composition as a function of the fragrance composition digital representation.

BRIEF DESCRIPTION OF THE DRAWINGS

Other advantages, purposes and particular characteristics of the invention shall be apparent from the following non-exhaustive description of at least one particular method which is the object of this invention, in relation to the drawings annexed hereto, in which.

DETAILED DESCRIPTION OF THE INVENTION

This description is not exhaustive, as each feature of one embodiment may be combined with any other feature of any other embodiment in an advantageous manner.

European patent application EP20172487.9 is incorporated by reference herein.

It should be noted at this point that the figures are not to scale.

It should be noted here that a 'recognisability prediction method' can be considered as a simulation method, for a technical parameter, insofar as a value representative of a technical parameter is the output of said method. By technical parameter, it is understood that such a parameter is representative of a force of nature.

The fragrance ingredient or composition spatial recognisability prediction method to prepare a fragrance composition comprising said fragrance ingredient or composition, comprises, in a minimal embodiment, the steps of:

- selecting, upon a computer interface, a value representative of between one and two of the following parameters:
  - a minimum sensory intensity level, corresponding to a predetermined minimum psychophysical intensity for the ingredient,
  - a maximum distance, corresponding to a distance at which the ingredient is to be perceived at a minimum predetermined psychophysical intensity level or
  - a quantity of the ingredient in liquid phase,
- wherein the selected value is selected within a range of at least two distinct values,
- computing, by a computing system, a value representative of either one of the following parameters:
  - a minimum sensory intensity level, corresponding to a predetermined minimum psychophysical intensity for the ingredient,
  - a maximum distance, corresponding to a distance at which the ingredient is to be perceived at a minimum sensory intensity level selected or set by default, preferably corresponding to the spatial dilution allowed by such sensory intensity level at the default settings for ingredient or composition quantity applied by the wearer, where it is applied, and the walking speed or
  - a quantity of the ingredient in liquid phase and
- wherein the computed value is representative of a parameter other than the parameter associated with the selected value and wherein a value for the parameter neither selected nor computed is set to a default value, said ingredient digital identifier corresponding to a physical ingredient to be used within a fragrance composition to be prepared as a function of the computed and selected values.

Such an embodiment is instantiated in the description of FIGS. 2 to 11 below.

Figure 2:
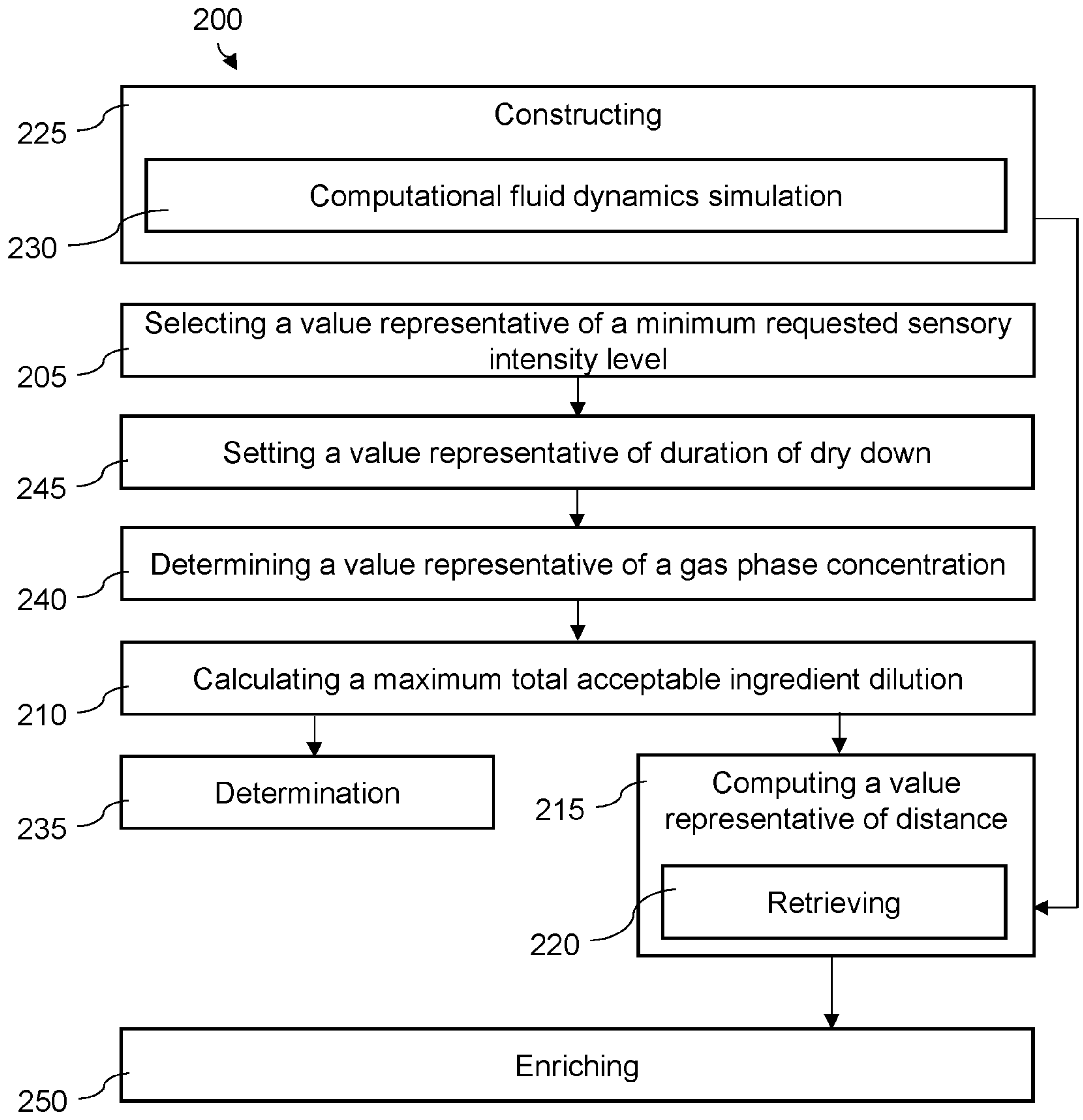
FIG. 2 represents, schematically and in the form of a flowchart, a first particular succession of steps of the method which is the object of the present invention.

FIG. 2 shows a particular succession of steps of a method which is the object of this invention. This fragrance ingredient or composition spatial recognisability prediction method 200 to prepare a fragrance composition comprising said fragrance ingredient or composition, comprises, in a minimal embodiment, the steps of:

- selecting 205, upon a computer interface, a value representative of a minimum requested sensory intensity level, corresponding to a desirable predetermined perceived minimum psychophysical intensity for the ingredient, said value being selected within a range of at least two distinct values,
- determining 240, by a computing system, a value representative of a minimum gas phase concentration of the ingredient corresponding to the selected minimum sensory intensity level as a function of a dose-response curve linking gas phase concentration to the selected minimum sensory intensity,
- calculating 210, by a computing system, a maximum total acceptable ingredient dilution, for both in gas and liquid phases of the fragrance, as a function of the determined minimum gas phase concentration and
- computing 215, by a computing system, at least one value representative of a distance from the fragrance source, up to a maximum distance from the fragrance source, at which the ingredient presents at least the minimum sensory intensity level selected as a function of the maximum total ingredient dilution calculated, said computing step comprising a step of retrieving 220, from an electronic storage, at least one value representative of the minimum spatial dilution for an ingredient in the gas phase corresponding to a predetermined downstream distance from the fragrance source, and preferably at the default settings for ingredient quantity applied by the wearer, where it is applied, and the walking speed.

The step of selecting 205 can be performed manually or automatically upon the considered computer interface. For example, in a particular embodiment, the step of selecting 205 is performed by a human operator handling a mouse and/or keyboard to input the selected minimum sensory intensity level desired for the ingredient upon a GUI of a software running on a computing system.

The selected minimum sensory intensity level should correspond to a desired performance of the ingredient aligned with consumer preferences and consumer use habits. A higher selected value corresponds to a more restrictive intended olfactory perception level that requests higher performance from the fragrance composition or ingredient. In particular embodiments of this invention, the minimum sensory intensity level can correspond, for example, to the recognition threshold for an ingredient under consideration. In particular embodiments of this invention, different minimum sensory intensity levels can be chosen for different ingredients in a fragrance composition.

The minimum sensory intensity level corresponds, for example, to a value of perceived psychophysical intensity for an ingredient such as defined by dose-response curves (for example in FIG. 1) and then, in turn, to a value of the gas-phase concentration of the ingredient.

In the prior art, such as disclosed in WO 2006/138726, the relationship between perceived psychophysical intensity and gas phase concentration for an ingredient is considered to be linear. Such a consideration brings the inventors to the use of a linear regression to establish this relationship. However, such a relationship has been found by the inventors of the present invention to be inferior in terms of predictive accuracy.

Other models could make use of the content of the disclosure Method for Predicting Odor Intensity of Perfumery Raw Materials Using Dose-Response Curve Database—KAO CORP—Hideki Wakayama, Mitsuyoshi Sakasai, Keiichi Yoshikawa, and Michiaki Inoue, Ind. Eng. Chem. Res., 58, 15036-15044, 2019. Such a disclosure provides dose-response curve for 314 perfumery raw materials.

In more advanced embodiments, a range or a set of minimum sensory intensity levels is selected, not necessarily same for all ingredients in a composition. In such embodiments, the steps of calculating 210 and computing 215 can be performed, as described below, for each value of the set of selected values or for the boundaries of the selected range of values.

In particular embodiments, the method 200 object of the present invention comprises a step of setting (not represented) a value representative of a liquid phase quantity of the ingredient applied on the body of the wearer such as by a spray dispenser that is linked to the surface area over which the ingredient is applied (therefore located at the fragrance source).

Such a step of setting can be performed in a similar manner to the step of selecting 205. In such embodiments, the gas phase concentration of the compound is linked to the liquid phase quantity via the equations of transport phenomena, including momentum conservation equations (such as Reynolds-Averaged Navier Stokes equations for the treatment of turbulent flow) and mass conservation equations, which can be computed and stored in an electronic storage as described in more detail below.

The step of determining 240 is performed, for example, by a computing system configured to execute a computer program calculating, based upon the parameters of a mathematical formula describing the dose-response curve, a value representative of the gas phase concentration corresponding to the selected minimum sensory intensity level.

In particular embodiments, the method 200 object of the present invention comprises a step of accessing (not represented) a database of dose response curve mathematical parameters, representing the key parameters of the mathematical formula describing the dose-response curve. In such embodiments, such mathematical parameters are used during the step of determining.

The step of calculating 210 is performed, for example, by a software executed by the computing system. This software may execute an algorithm linking requested perceived psychophysical intensity (sensory intensity) of an ingredient in the fragrance trail to the maximum spatial dilution of said ingredient in the fragrance trail. For fragrance compositions, the algorithm also uses values representative of the composition of the fragrance at a chosen time in the dry down (time elapsed from fragrance application on the wearer) such as a weight fraction of the ingredient and, optionally, values representative of the activity coefficients of ingredients for the given fragrance composition.

For example, during this step of calculating 210, the following mathematical formula may be used:

$$y=5{,}1696x^2+13{,}507x$$

Where:

- y corresponds to a dimensionless spatial dilution factor, which is the ratio of the maximum headspace concentration at distance zero (at the liquid-air interface of the fragrance) to the maximum headspace concentration at a distance x from the fragrance source, and
- x represents a distance, in centimetres, from a fragrance source in a scaled-down model presenting a geometric similarity to human-scaled system with an airflow rate of 1 m/s.

In the context of the current invention, 'maximum total dilution', also called 'Odor Dilution Capacity' (ODC), refers to the ratio of the equilibrium (saturation) gas phase concentration (or volatility) of the ingredient at a given temperature to the gas phase concentration of said ingredient corresponding to the minimum sensory intensity level requested for said ingredient. The higher the maximum total dilution value, or ODC, of the ingredient the more tolerant the ingredient is to spatial dilution and thus the farther away from the fragrance source the ingredient can be perceived at or above the minimum sensory intensity level specified, for a given liquid-phase dilution. Equivalently, to be perceived a fixed distance from the fragrance source at or above the minimum sensory intensity level, the higher the ODC of the ingredient the more it can be diluted in the liquid phase.

For a single (pure) ingredient, maximum spatial dilution is same as maximum total dilution (i.e. the ODC, defined above), and it is a function of an intended intensity level at which said ingredient is to be perceived. For an ingredient that is part of a mixture, such as a fragrance composition, maximum spatial dilution is calculated from maximum total dilution by using relative dosage of the ingredient in the composition at a chosen time in the dry down (time elapsed since the fragrance is applied on the wearer), for example its weight fraction, as well as optionally an activity coefficient (such as calculated from UNIFAC, Modified UNIFAC Dortmund, or similar activity coefficient models) to account for any non-ideality of the mixture, as appropriate.

The step of computing 215 at least one value representative of a distance (spatial) reach of an ingredient is performed, for example, by a software executed by the computing system, said software performing using an algorithm linking spatial dilution to downstream distance from the wearer (or, fragrance source) in the trail.

Such an algorithm can be constructed by a Person Skilled in the Art by empirical measurement of gas phase concentration of an ingredient at a predetermined distance from the source of said ingredient, located at its vapour-liquid interface, such as on the skin of the wearer, for a determined air flow intensity transporting the gaseous ingredient from the source (vapour-liquid interface) location to a sensor location. Alternatively, these values could be obtained from measurements in a wind tunnel type of experiment.

Alternatively, an algorithm linking spatial dilution to downstream distance from the source could be constructed from a highly approximative estimation approach utilising the Gaussian Plume type of model, borrowed from environmental engineering. However, such models are meant to be applied to much larger length scales, for example in miles or kilometres, such as those relevant to environmental contaminant transport, and do not address strong turbulent gas phase mixing due to the airflow around the human body, which is an essential feature of fragrance trail.

Figure 6:
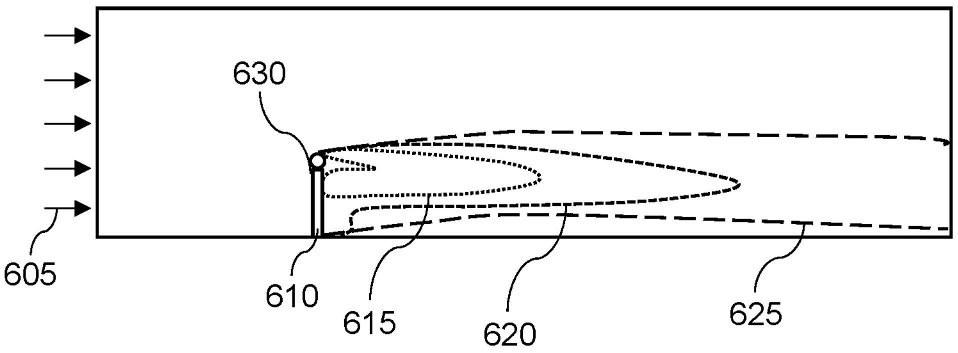
FIG. 6 represents, schematically, a graphical representation of the trail phenomenon in terms of spatial iso-dilution contours in the wake of a person wearing fragrance, extracted from a computational fluid dynamics simulation.

Alternatively, in a preferred embodiment, an algorithm linking spatial dilution to downstream distance from the source can be the product of digital modelling, such as described in the context of FIG. 6. In such an alternative, a spatial (gas phase) dilution factor value is related to a value of downstream distance from the fragrance source for a given (chosen) quantity of fragrance applied, or equivalently, for the surface area over which the fragrance is applied on a specific part of the body.

In a simple embodiment, such a link between spatial dilution and downstream distance from the fragrance source is achieved by a correspondence table matching downstream distance from the wearer to spatial (gas phase) dilution, the latter quantifying reduction in the gas phase concentration of an ingredient relative to its saturation gas-phase concentration at the liquid-air interface (at the source). For example, depending on a particular incident air flow velocity and surface area over which a fragrance is applied on the human body, a distance of one metre could be linked to a reduction in the interfacial gas phase concentration of a factor of at least 30, a distance of two metres to a reduction of a factor of at least 65 and a distance of three metres to a reduction of a factor of at least 100.

Knowing the maximum spatial dilution that can be applied to an ingredient (either pure or in a fragrance composition) while maintaining its perception level at or above the selected minimum sensory intensity level, the step of computing 215 determines the maximum downstream distance from the wearer where the minimum sensory intensity level is met.

In particular embodiments, such as the one illustrated in FIG. 2, the step of computing 215 comprises a step of retrieving 220, from an electronic storage, at least one value representative of the minimum spatial dilution for an ingredient in the gas phase corresponding to a predetermined downstream distance from the fragrance source, said value being used to compute the maximum downstream distance from the fragrance source at which the ingredient presents at least the minimum sensory intensity level selected.

The step of retrieving 220 is performed, for example, by a communication medium commanded by a network card of the computing system. Such a communication medium can be an antenna or a wire link to a communication network (the Internet, for example). Alternatively, the electronic storage is an electronic memory attached to or part of the computing system, such as a hard drive, for example.

During this step of retrieving 220, the computing system establishes a connection to the electronic storage to extract the requested values. Such downstream distance to spatial dilution functional relationships are then used in the step of computing 215.

In particular embodiments, such as the one illustrated in FIG. 2, the method 200 object of the present invention comprises, prior to the step of retrieving 220, a step of constructing 225 a minimum spatial dilution electronic storage, said step of constructing matching minimum spatial dilution values to at least one distance from a fragrance source value and at least one of the following indicators:

- an indicator representative of an incoming air flow velocity incident upon the fragrance source comprising said ingredient,
- an indicator representative of an ingredient or fragrance composition application surface area,
- an indicator representative of simulation parameters for the shape of a human body and/or
- an indicator representative of area location on a human body upon which the ingredient or fragrance composition is applied, said step of constructing comprising a step of computational fluid dynamics simulation 230 configured to calculate said spatial dilution values at predetermined downstream distances from the source.

The step of constructing 225 can be performed by a computing system running a computational fluid dynamics simulation software, setting up a model based on a plurality of input parameters, including specific dimensions and approximate but realistic geometric details of a human body, performing the step of computational fluid dynamics calculation 230, performing post-processing analysis of the raw data from the calculation to reduce data dimensions from 3 dimensions to 1 dimension (distance), and storing the computed values in the electronic storage.

Such geometric details of a human body can be the position of the head or the size and the shape details of the head, torso or arms, for example.

The step of computational fluid dynamics simulation 230 makes use, for example, of Menter's Shear Stress Transport turbulence model. To keep the simulation tractable, the simulation is preferably performed on a stationary mesh, such that the air is preferably moving to the average speed of interest (for example, the average walking speed of 1.4 m/s) and in the direction incident on the front of the human body (for example, in the direction outward normal to the back of the human body or, equivalently, in the direction opposite to the outward normal to the frontal plane of the human body such as chest) while the human is kept stationary. First, air flow velocity distribution in space, also known as the air flow velocity vector field, is calculated in three dimensions around the human body from the aforementioned turbulence model. Then, fragrance transport in the air is simulated in three dimensions accounting for convection (utilising pre-calculated air flow velocity vector field in three dimensions from the previous step) and diffusion (including turbulent diffusivity) for a plurality of predetermined fragrance application surface areas and fragrance application locations on the human body, chosen to represent realistic consumer habits of fragrance wear.

Figure 12:
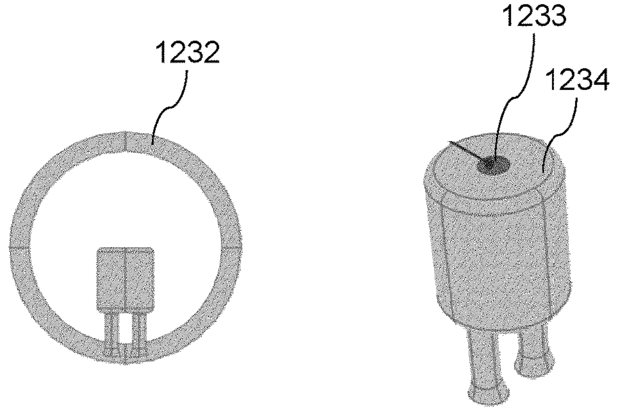
FIG. 12 represents, schematically, a simplified computational fluid dynamics simulation environment of a scale model that is related to the context of the present invention.

A simulation environment relative to said computational fluid dynamics simulation 230 can be seen as matter of illustration in FIG. 12. In this oversimplified scale model of fragrance trail 1234, a fragrance source 1233 is located at the top surface (3 square centimetre in the example below), said model 1234 being located within a tube 1232 in which airflow is directed at the model 1234 in a direction aligned with the axis of symmetry of the tube without employing any vorticity-inducing upstream mixing means such as a fan.

The output of such a step of computational fluid dynamics simulation 230 in the environment of FIG. 12 is, for example:

| x, downstream distance from source (cm) | max headspace concentration, c_max_x (ug/L) | Spatial dilution factor = c_max_0/c_max_x |
|---|---|---|
| 0.0 | 1436.39 | 1 |
| 0.5 | 539.50 | 2.66 |
| 1.5 | 54.66 | 26.28 |
| 2.0 | 29.94 | 47.98 |
| 2.5 | 20.83 | 68.97 |
| 3.0 | 15.82 | 90.80 |
| 4.0 | 10.52 | 136.57 |
| 5.0 | 7.35 | 195.33 |

Figure 14:
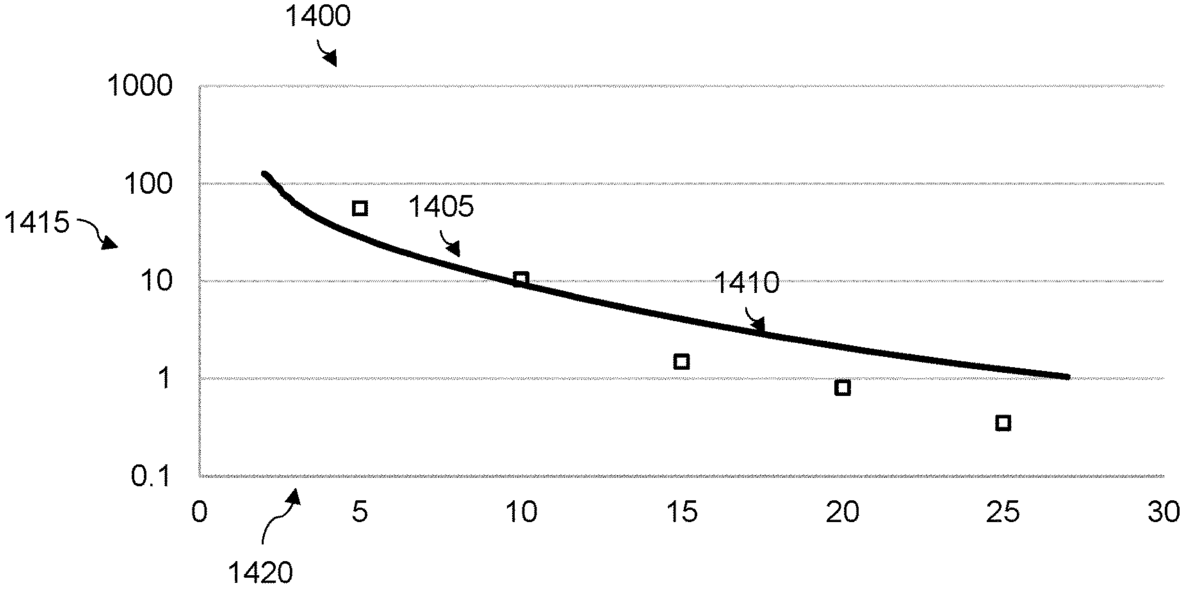
FIG. 14 represents, schematically, a comparison for simulated computational fluid dynamics and actual measurement

FIG. 14 represents, schematically, a graph 1400 showing:

- a curve 1405 representing simulated computational fluid dynamic modelling results,
- actual measurements 1410 in a real-life, similar system to the system modelled by the curve 1405,
- in the x-axis 1420, a distance in centimetres from the liquid-gas interface of a chemical compound and
- in the y-axis 1415, a gas phase concentration (in micrograms/litre) of the chemical compound.

FIG. 6 represents, schematically, a plot of the results of such a step of computational fluid dynamics simulation 230 where:

- reference 605 represents the air flow rate projected upon a human model 610 wearing an ingredient or a fragrance composition of predetermined application surface area and at a specified location on the body and
- references 615, 620 and 625 represent isolines, i.e. contour lines tracing out constant gas phase concentrations chosen from within the range of computed values where the first isoline 615 represents the highest gas phase concentration, a second isoline 620 represents an intermediate gas phase concentration and a third isoline 625 represents the lowest gas phase concentration from the values chosen to be represented by the contour lines.

Alternatively, these isolines, 615, 620 and 625, may designate contour lines of constant spatial dilution factors chosen from within the range of computed values, the dilution factor being calculated by the division of the maximum gas phase concentration of an ingredient, which is the interfacial concentration of the chosen fragrance ingredient (in other words, its saturation gas-phase concentration at a given temperature, related to its vapour pressure, or partial vapour pressure if part of a mixture in the liquid phase, at same temperature via the ideal gas law), at the location 630 where the ingredient is worn on the body, by the gas phase concentration at the particular spatial coordinates considered within the fragrance trail.

It is clear from FIG. 6 that gas-phase fragrance concentrations and associated spatial dilutions (equivalently, spatial dilution factors) in the trail exhibit complex spatial variations that are substantial and non-linear in the downstream direction from the human model. Similarly, complex spatial variations in gas-phase concentrations and associated spatial dilution factors also exist over cross-sectional planes (not shown) perpendicular to the direction of the incoming air flow (i.e. perpendicular to the plane shown in FIG. 6). At each downstream distance from the human model, the maximum gas-phase fragrance concentration (equivalently, the minimum gas-phase dilution factor) can be extracted from the full three-dimensional solution. The result of this approach is a practical and tractable interpretation of fragrance trail in terms of a one-to-one relationship between gas phase (spatial) dilutions in the trail and downstream distances from the person wearing fragrance.

This analysis can be performed at different ingredient or fragrance placement on the body, such as but not limited to the neck, shoulders or both, for example. This analysis can be performed at different surface areas of the ingredient or fragrance composition on the human body. This analysis can also be performed at different incoming air velocities.

Performance of fragrance compositions, whether linked to trail or to other performance attributes that may be defined in the prior art, is typically considered in terms of olfactive performance metrics of constituent ingredients.

In the prior art, Odor Value has been the de facto standard olfactive performance metric for odorous compounds, utilised for both performance-based ingredient selection and for estimation of ingredient performance in formulation.

Odor Value of an odorous ingredient is defined as a dimensionless ratio of its volatility, which is the equilibrium (interfacial) gas-phase concentration at saturation (usually at a temperature in the range of 20-40° C., but other temperatures can be used), and its odour detection threshold (ODT), which is the lowest gas-phase concentration at which the ingredient is detectable by the human nose: Odor Value=$c_{g,interf}/c_{g,ODT}$, where $c_{g,interf}$ is the interfacial gas-phase concentration of an ingredient at saturation (or, its volatility), which can be derived from an ideal gas law and either the vapour pressure (pure ingredient) or partial pressure (for ingredient in a composition), and $c_{g,ODT}$ is the ODT as explained above.

The deficiency of Odor Value as a metric for fragrance performance is two-fold.

First, since the Odor Value is based on the odour detection threshold, any ingredient performance metric based on the Odor Value requires only that the ingredient is present in the gas phase at least at its odour detection sensory level but does not predict whether the ingredient will elicit a strong or a weak perception at realistic usage levels in fragranced consumer products. Therefore, this odour detection criterion, while necessary, is not a sufficient one for designing fragrance products with desirable performance that meet or exceed consumer expectations. Due to insufficiency of the underlying sensory perception criterion, Odor Value-based performance metrics overstate ingredient performance, including in formulations (compositions), and imply that ingredients could be used at lower amounts than actually needed to provide a requested level of sensory performance (for example, certain minimum sensory intensity or recognition).

Figure 1:
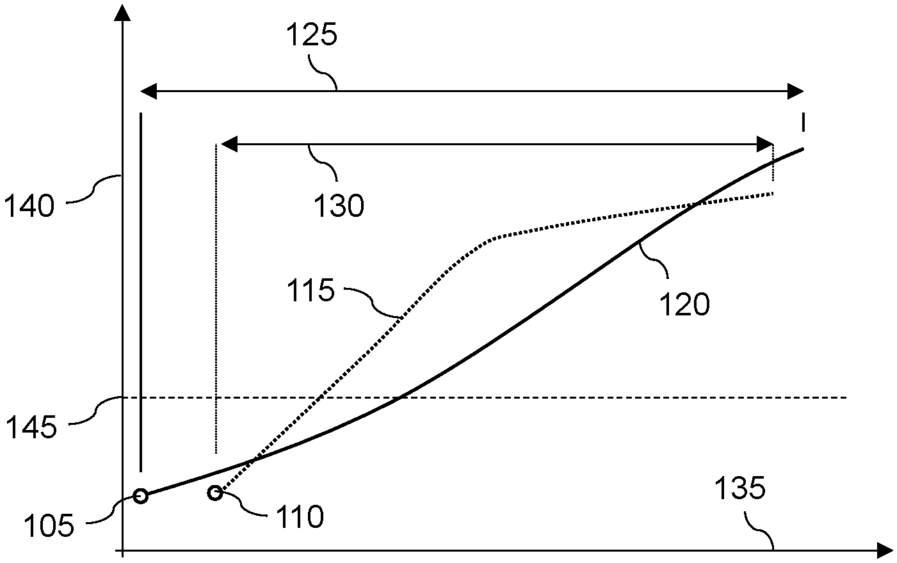
FIG. 1 represents, schematically, the dose-response curve for two particular fragrance ingredients.

Second, when comparing performance of different ingredients, performance metrics based on Odor Value are not predictive of relative ingredient performance at perceived intensities generally linked to desired fragrance performance in various consumer product applications. FIG. 1 illustrated this point using dose-response curves for alpha damascone and delta damascone, where a crossover in relative performance is observed while increasing gas-phase concentrations from detection level (ODT) to medium-intensity levels. In other words, olfactory dose-response characteristics provide a significantly more accurate and reliable description of sensory performance of odorous ingredients than does odour detection threshold (or Odor Value, which is based on detection threshold) in real conditions of fragrance wear and use by consumers. The extent of erroneous performance overestimation stemming from the use of Odor Value-based performance metrics will be illustrated below.

In the method object of the present invention, performance of constituent ingredients in fragrance compositions is linked to their spatial reach in the trail, which is defined as the maximum downstream distance from the fragrance wearer at which minimum required sensory intensity of the ingredient is achieved, by defining and evaluating Odor Dilution Capacities (ODCs) of said ingredients, which, unlike the Odor Value, are defined based on a realistic sensory performance criterion linked to consumer fragrance wear and consumer use of fragranced products.

Figure 7:
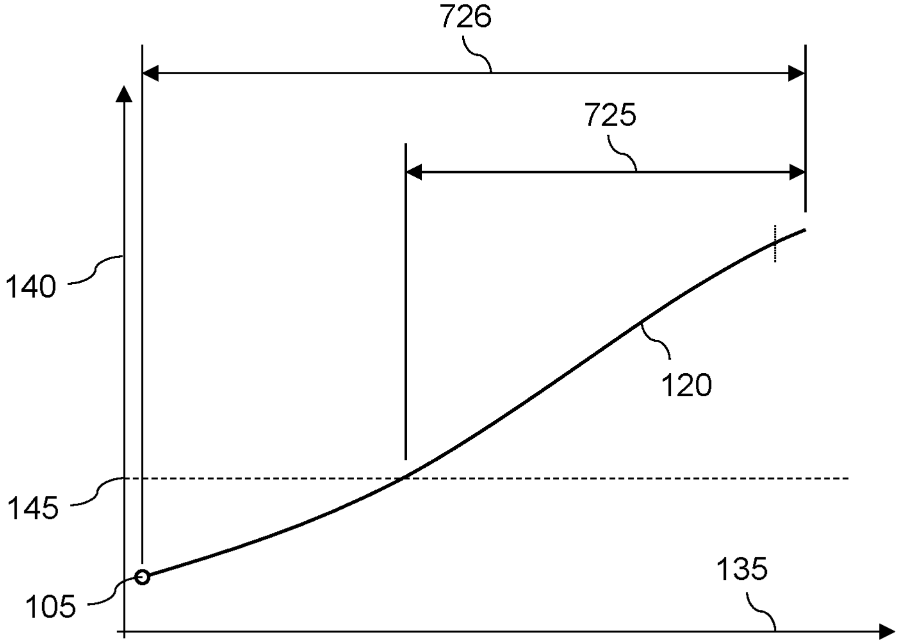
FIG. 7 represents, schematically, a graphical representation of the Odor Dilution Capacity of a fragrance ingredient (compound) compared to Odor Value for same ingredient.

Odor Dilution Capacity of an odorous ingredient can be defined as $c_{g,interf}/c_g(\text{Iref})$, where $c_{g,interf}$ is the interfacial gas-phase concentration of a pure ingredient at saturation at a chosen fixed reference temperature (which is mathematically related to the vapour pressure), and $c_g(\text{Iref})$ is the gas-phase concentration of an ingredient at a minimum required sensory intensity level Iref selected for specific requirements of ingredient or fragrance performance in a given consumer product (i.e., a specific sensory intensity that may be linked to, for example, recognition of an ingredient or fragrance composition). FIG. 7 illustrates the definition of ODC and shows graphically on an example dose-response curve the difference between the ODC 725 approach of the current invention and the classical Odor Value 726 approach of the prior art.

FIG. 7 shows a graphical representation of the ODC 725 value for delta damascone based upon the selected minimum sensory intensity level 145.

It should be noted that the ODC metric can be readily adjusted to adapt to sensory performance requirements of a particular consumer product application by changing the Iref criterion, which is the minimum sensory intensity requested in a given consumer product application or for a given ingredient. On the other hand, in the Odor Value approach of the prior art, such capability is not possible because the only level of sensory performance that is accessible by such approach is the odour detection. As such, Odor Value applies the most liberal possible sensory performance criterion possible for quantifying performance of fragrance ingredients, and, for this reason, it considerably overstates performance capabilities of fragrance ingredients, both pure and in compositions.

Figure 11:
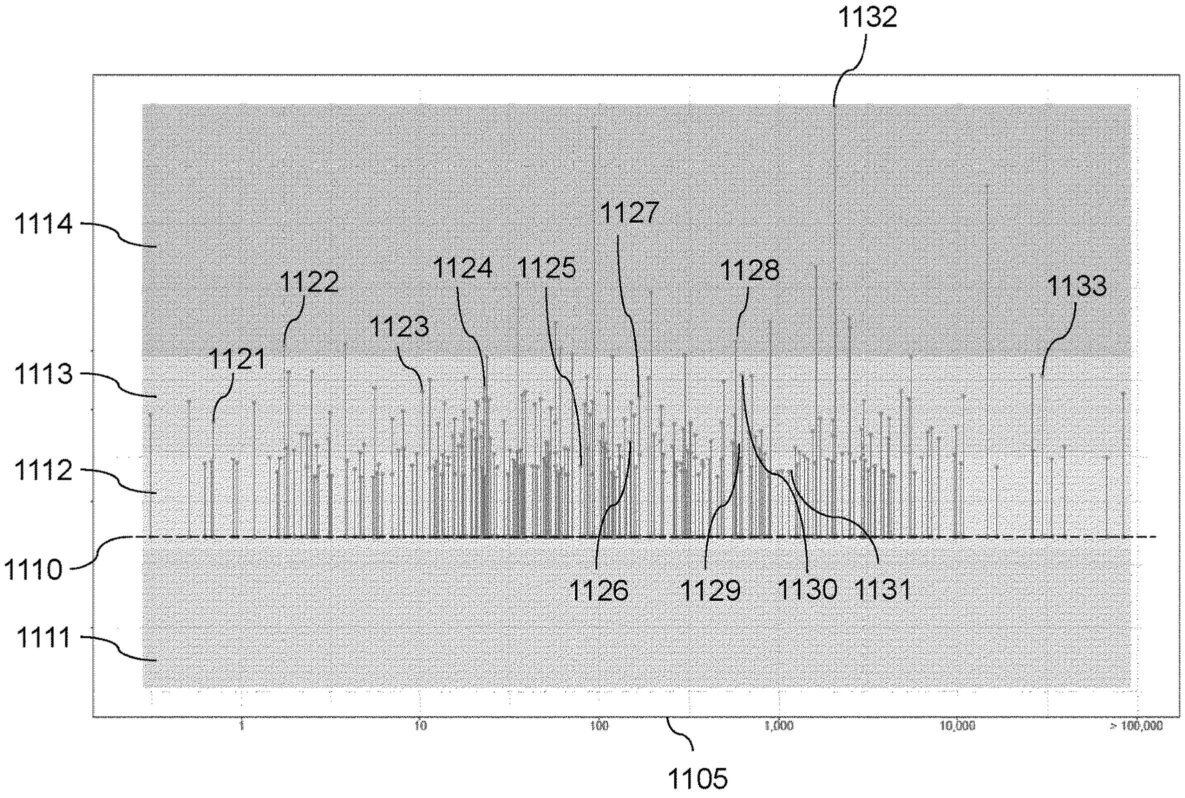
FIG. 11 represents, schematically, the relationship between volatility, spatial reach (recognisability) based on odour value (odour detection threshold) and spatial reach (recognisability) based on odour dilution capacity (ODC) for a number of ingredients.

FIG. 11 shows, schematically, a graph representing, on the x-axis 1105, the volatility of a finite number of ingredients and, on the y-axis several ingredient recognisability ranges, which are linked to the distance (from fragrance source) at which the ingredient is to be perceived, clustered into the following categories:

near skin (or near the source or substrate) 1111,
aura (up to 0.5 metres from source) 1112,
trail (up to 4 metres from source) 1113 and
room filling (more than 4 metres from source) 1114.

The liquid-phase fraction (liquid-phase dilution) of each ingredient shown in FIG. 11 has been chosen to yield the same level of recognisability 1110 (y-axis) that is computed from the ODC performance metric such as disclosed in the present application. Each vertical line in FIG. 11 represents an ingredient and connects vertically the recognisability level 1110 for said ingredient determined from the ODC performance metric with the recognisability level for said ingredient determined from the Odor Value performance metric of the prior art, indicated for example by points labelled 1121-1133.

FIG. 11 shows that the Odor Value-based metric of the prior art substantially overestimates recognisability (distance reach) of a large plurality of fragrance ingredients without any specific pattern, indicating a substantial deficiency of the methods of the prior art that rely on the odour detection threshold and Odor Value concepts. Since the Odor Value-based metric references odour detection only, it often grossly overestimates spatial reach (recognisability) of ingredients as opposed to the ODC metric disclosed in the current invention, which references finite perceived intensities from the dose-response characteristics of ingredients that are linked to real conditions of trail and consumer use.

The table below identifies some of the ingredients on the chart of FIG. 11, where their spatial performance in terms of spatial recognisability is substantially overestimated by the methods currently known in the art.

Therefore, once the minimum sensory intensity level criterion is selected, the corresponding maximum gas-phase dilution of a fragrance ingredient that satisfies this sensory criterion allows estimation of spatial reach of said ingredient in the trail (i.e. maximum downstream distance from the fragrance wearer at which the sensory criterion is satisfied). Although this maximum gas-phase dilution of a fragrance ingredient can be obtained from the Odor Value metric of the prior art, which uses mere odour detection rather than recognition or a specific sensory intensity as the sensory criterion for performance, the Odor Value metric both overstate ingredient performance and is not predictive of relative ingredient performance at sensory intensities associated with real consumer fragrance wear and product usage habits. Therefore, most preferably, and as a significant improvement over the prior art, maximum gas-phase dilution of a fragrance ingredient is obtained from the Odor Dilution Capacity metric of the current invention, which utilises realistic sensory intensities encountered in consumer product applications, associated with consumer fragrance wear and usage habits, as the sensory criteria for targeted fragrance performance.

To calculate the ODC, sensory dose-response characteristics, which could be provided as parameters of a mathematical expression describing sensory intensity as a function of gas-phase concentration, for constituent ingredients of a fragrance formulation are necessary, as well as vapour pressures or volatilities of those ingredients and desired sensory intensity level Iref as the sensory criterion for the minimum sensory performance level (which could in some particular embodiments be linked to recognition or recognition threshold), where Iref could be chosen from a set of values or even set individually for each ingredient.

Olfactory dose-response data for approximately several hundred odorous ingredients has been published in the public domain by the Kao Corporation, to mention one known example, such as disclosed above.

| Reference | CAS | Chemical (IUPAC) Name |
|---|---|---|
| 1121 | 31906-04-4 | (+−)-3/4-(4-HYDROXY-4-METHYLPENTYL)-3-CYCLOHEXENE-1-CARBALDEHYDE |
| 1122 | 198404-98-7 | [1-METHYL-2-[(1,2,2-TRIMETHYL-3-BICYCLO[3.1.0]HEXANYL)METHYL]CYCLOPROPYL]METHANOL |
| 1123 | 31983-27-4 | 3,7-DIMETHYLOCTA-2,6-DIENENITRILE |
| 1124 | 107-75-5 | (+−)-7-HYDROXY-3,7-DIMETHYLOCTANAL |
| 1125 | 19870-74-7 | (+−)-8-METHOXY-2,6,6,8-TETRAMETHYL-TRICYCLO[5.3.1.0(1,5)]UNDECANE |
| 1126 | 2563-07-7 | 2-ETHOXY-4-METHYLPHENOL |
| 1127 | 103-93-5 | (4-METHYLPHENYL) 2-METHYLPROPANOATE |
| 1128 | 90-05-1 | 2-METHOXYPHENOL |
| 1129 | 18479-58-8 | 2,6-DIMETHYL-7-OCTEN-2-OL |
| 1130 | 104-45-0 | 1-METHOXY-4-PROPYLBENZENE |
| 1131 | 13254-34-7 | 2,6-DIMETHYL-2-HEPTANOL |
| 1132 | 27043-05-6 | 2-ETHYL-3,(5 OR 6)-DIMETHYLPYRAZINE |
| 1133 | 98-02-2 | 2-FURANMETHANETHIOL |

Computational fluid dynamics simulation results, discussed above, link downstream distance in the trail of the fragrance wearer with gas phase (spatial) dilution of a fragrance ingredient or fragrance composition, emitted from a walking human, for real fragrance wear parameters linked to consumer wear habits and fragrance use. Combining compositional information about a fragrance (such as relative quantities of constituent ingredients) at a given time from fragrance application on the wearer and the ODC values for constituent ingredients of said fragrance, sensory performance of the fragrance at a desired distance in the trail can therefore be predicted from such a relationship between distance and spatial dilution computed for any combination of desirable fragrance wear parameters.

Vapour pressure can be obtained from physical property databases such as but not limited to DIPPR (American Institute of Chemical Engineers), Dortmund Data Bank (DDBST GmbH), PHYSPROP (Syracuse Research Corporation), or DETHERM (DECHEMA) or predicted with freely available software tools such as but not limited to EPISuite (US Environmental Protection Agency).

In particular embodiments, such as the one illustrated in FIG. 2, the method 200 object of the present invention comprises a step of setting 245 a value representative of a duration of dry down (i.e., time elapsed from initial product application on the wearer) of the ingredient or composition containing said ingredient, the step of computing 215 of a value representative of a distance from the fragrance source being achieved as a function of the duration of dry down set.

This value can typically be set within the range of 0 to 360 minutes but could extend to any length of time relevant to the useful life of a fragrance in a consumer product of interest.

This step of setting 245 can be performed manually or automatically upon a computer interface. For example, in a particular embodiment, the step of setting 245 is performed by a human operator handling a mouse and/or keyboard to input a desired dry down duration for the ingredient upon a GUI of a software running on a computing system.

The set time is representative of a duration of evaporation of the ingredient from liquid phase to gas phase, such ingredient being transported away from the fragrance source by airflow. Depending on the duration of dry down, the quantity of a given ingredient in air can be known by using evaporation kinetics formulas.

The duration of dry down can either reduce or increase the maximum gas phase concentration at the location of the ingredient in a fragrance composition, depending on the volatility of said ingredient and on the volatility and relative quantities of other ingredients in the fragrance composition. For ingredients with higher volatilities in a fragrance composition, such as top notes and certain middle (heart) notes, the gas-phase concentration and corresponding spatial reach will decrease monotonically over time elapsed from fragrance application on the wearer. However, for ingredients such as the bottom (base) notes, which have the lower or lowest volatilities in a composition, their relative contribution in the formula actually increases over time elapsed from fragrance application, as the more volatile ingredients leave the formula, also increasing the gas-phase concentration and trail performance for those lower-volatility ingredients.

In particular embodiments, such as the one represented in FIG. 2, the method 200 object of the present invention comprises a step of enriching 250 an ingredient digital identifier database.

This step 250 of enriching is performed, for example, by a computing system executing a software configured to determine the change in perceived intensity anchored around a desired sensory intensity level as a function of a predetermined spatial ingredient dilution factor (ratio). This change in perceived intensity as a result of specified ingredient dilution ratio in the gas phase is hereby defined as 'resistance to dilution', and the result of this calculation is preferably stored in an electronic storage in correspondence to the ingredient digital identifier.

Resistance to dilution of an ingredient is calculated from the change in perceived intensity over, for example, 20-fold gas-phase dilution in the vicinity of the selected minimum perceived intensity level, but it is not limited to this specific gas-phase dilution factor and can be adjusted based on intended consumer use of the fragranced product and/or the product format.

In particular embodiments, such as the one represented in FIG. 2, the step of enriching 250 an ingredient digital identifier database is configured to determine and store, based upon the calculated resistance to dilution (noted 'ΔI' or as a specific example '□I20X' if the dilution factor is 20) and ODC values linked to various minimum sensory intensity levels, additional relevant ingredient performance metrics, which may be derived from performance metrics already described and may also integrate other ingredient information such as cost, for example. Enrichment of the digital ingredient identifier database in such a way has the practical benefit of intelligent fragrance design, guiding selection and dosage optimisation of ingredients based on their performance in the trail as well as other attributes relevant to fragrance design, such as cost, all of which lead to improvements in consumer products where such fragrances are incorporated.

Figure 3:
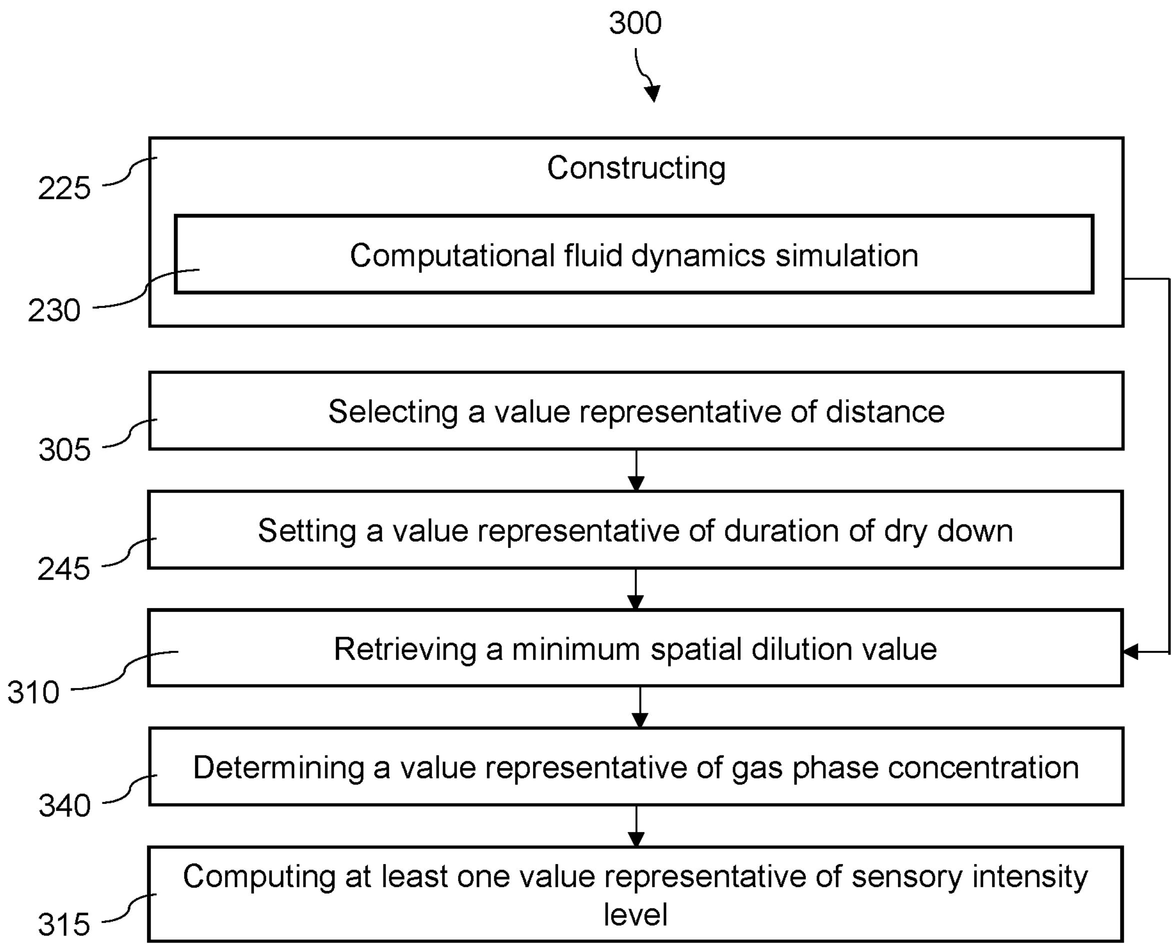
FIG. 3 represents, schematically and in the form of a flowchart, a second particular succession of steps of the method which is the object of the present invention.

FIG. 3 shows a particular succession of steps of a method which is the object of this invention. This fragrance ingredient or composition spatial recognisability prediction method 300 to prepare a fragrance composition comprising said fragrance ingredient or composition, comprises the steps of:

- selecting 305, upon a computer interface, a value representative of a distance within a range of at least two distinct values and up to a maximum downstream distance from the fragrance source at which the ingredient presents a minimum sensory intensity level corresponding to a predetermined minimum psychophysical intensity for the ingredient,
- retrieving 310, from an electronic storage, a minimum spatial dilution value associated with the selected distance,
- determining 340, by a computing system, a value representative of gas phase concentration of the ingredient corresponding to the spatial dilution value retrieved and
- computing 315, by a computing system, for the selected value of distance, at least one value representative of a sensory intensity level as a function of a dose-response curve linking gas phase concentration to sensory intensity level.

The step of selecting 305 can be performed manually or automatically upon the considered computer interface. For example, in a particular embodiment, the step of selecting 305 is performed by a human operator handling a mouse and/or keyboard to input the maximum distance desired for the ingredient upon a GUI of a software running on a computing system.

The maximum selectable distance should correspond to a maximum spatial reach of the ingredient in the trail downstream from the wearer, over which the minimum sensory intensity criterion is met. Selecting a distance higher than this maximum leads to a violation of the specified minimum sensory intensity criterion.

In particular embodiments, the method 300 object of the present invention comprises a step of setting (not represented) a value representative of a liquid phase quantity of the ingredient in addition to the selected distance. Such a quantity is an absolute quantity of the liquid product applied on the wearer and is used in determining the maximum selectable distance for each ingredient for a specified minimum sensory intensity criterion.

Such a step of setting can be performed in an analogous manner to the step of selecting 305. The step of retrieving 310 is performed, for example, by a software executed by the computing system, said software using an algorithm linking distance to spatial dilution.

In this context, 'maximum total dilution', also known as the ODC defined above, refers preferably to the difference, quantified as a ratio, between the maximum (saturation) gas phase concentration (or, volatility) of the ingredient for a given temperature and the gas phase concentration corresponding to the minimum sensory intensity level selected. The higher the maximum total dilution value (or, the ODC), the more robust the ingredient is to spatial dilution and thus the farther away the ingredient can be perceived at the selected minimum sensory intensity for a given quantity of the liquid phase applied on the wearer.

The step of determining 340 is performed, for example, by a computing system configured to execute a computer program. During this step of determining 340, a value for gas phase concentration, or gas phase concentration variation, is obtained by the use of the results of a model linking distance to dilution, such as one obtained in regards to the description of FIG. 6.

In embodiments comprising a step of setting an initial liquid phase quantity, the liquid phase quantity at different times in the dry down (i.e., time elapsed from application of the ingredient on the wearer) can be calculated through an evaporation rate of the liquid phase related to the volatility of the given ingredient. The relationship between evaporation rate and volatility can be obtained by empirical measurement or by simulation utilising computational fluid dynamics and by subsequent construction of an electronic storage of evaporation rates for pure ingredients at a temperature of interest, for example.

The step of computing 315 of at least one value representative of a sensory intensity level is performed, for example, by a software executed by the computing system, said software performing using an algorithm linking gas phase concentration to the sensory intensity level. Such a step of computing 315 may use the dose-response curve of the ingredient, or parameters representing the mathematical formula of said dose response curve, to determine said perceived sensory intensity level.

It should be understood that the embodiment of FIG. 3 may comprise all the variations of the embodiment of FIG. 2 relative, in particular, to the steps of retrieving 220, constructing 225, computational fluid dynamics simulation 230, determining 245 a value representative of duration of dry down, enriching 250 a database, calculating 255 and/or construction 260 of a resistance to dilution value.

Figure 4:
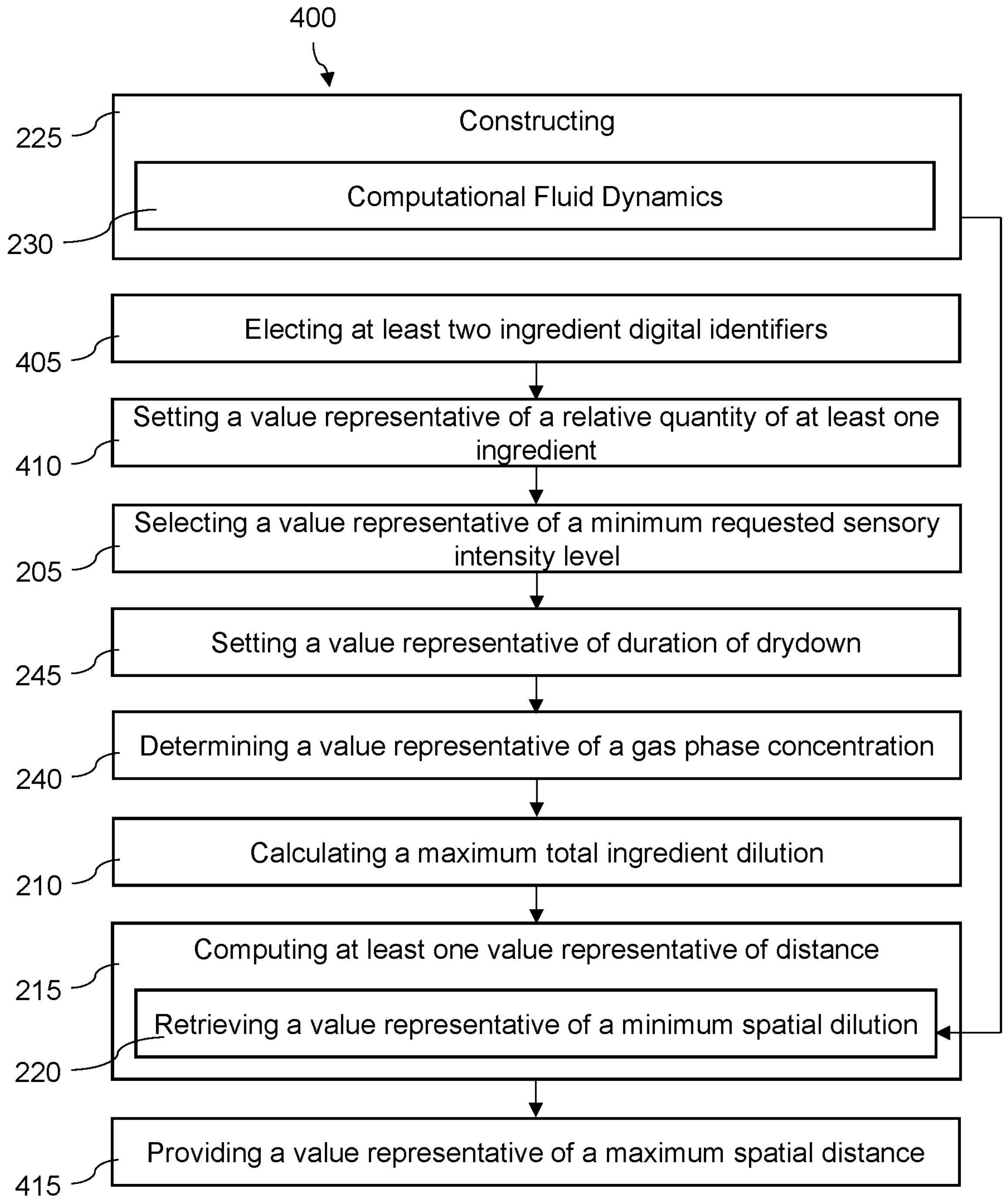
FIG. 4 represents, schematically and in the form of a flowchart, a third particular succession of steps of the method which is the object of the present invention.

FIG. 4 shows a particular succession of steps of a method which is the object of this invention. This fragrance composition spatial recognisability prediction method 400 to prepare a fragrance composition comprising said fragrance ingredient or composition, comprises the steps of:

- electing 405, upon a computer interface, at least two ingredient digital identifiers to form a fragrance source,
- setting 410, upon a computer interface, a value representative of a relative quantity of at least one said ingredient identified by said digital identifier,
- selecting 205, upon a computer interface, a value representative of a minimum requested sensory intensity level, corresponding to a desirable predetermined perceived minimum psychophysical intensity for at least one ingredient, said value being selected within a range of at least two distinct values, preferably in which ingredients without an explicitly defined sensory intensity are assigned a default value such as the minimum of all assigned intensity levels of all the other ingredients present in the composition,
- determining 240, by a computing system, a value representative of a minimum gas phase concentration for each said ingredient corresponding to the selected minimum sensory intensity level as a function of a dose-response curve linking gas phase concentration to the selected minimum sensory intensity,
- calculating 210, by a computing system, a maximum total ingredient dilution, for both in gas and liquid phases of the fragrance, as a function of the determined minimum gas phase concentration, for each said ingredient and
- computing 215, by a computing system, at least one value representative of a distance from the fragrance source, up to a maximum distance from the fragrance source, at which at least one ingredient presents at least the minimum sensory intensity level selected as a function of the maximum total ingredient dilution calculated.

The step of electing 405 can be performed manually or automatically upon the considered computer interface. For example, in a particular embodiment, the step of electing 405 is performed by a human operator handling a mouse and/or keyboard to input the maximum distance desired for the ingredient upon a GUI of a software running on a computing system.

Such a step of electing 405 may consist of direct election, that is the selection of the ingredient identifiers represented as such upon an interface, for example, or indirect election, that is the selection of the ingredient identifiers via an intermediate digital object, such as an image or an icon representing the identifier.

The step of setting 410 can be performed manually or automatically upon the considered computer interface. For example, in a particular embodiment, the step of setting 410 is performed by a human operator handling a mouse and/or keyboard to input the maximum distance desired for the ingredient upon a GUI of a software running on a computing system.

The relative quantity selected can represent mass fraction or mole fraction in an ingredient composition of the fragrance.

This way, to predict performance of fragrance compositions in the trail via their constituent ingredients, a mixture law (the most common example of a mixture law being Raoult's Law for ideal mixtures) is applied to the ODC of each constituent ingredient. The reasoning is as follows: the ODC performance metric provides maximum total dilution of an ingredient while maintaining the sensory performance level at or above the selected minimum sensory intensity level. The maximum total dilution described by the ODC includes dilution in the liquid phase (i.e. defined by the relative quantity of each ingredient in a fragrance composition) and dilution in the gas phase. Dilution in the liquid phase is accounted for by multiplying ODC of the ingredient by its mass fraction also known as the weight fraction (or, more rigorously correct but less practically convenient, by its mole fraction) in composition. This is because, in a fragrance composition, the equilibrium (maximum) interfacial gas-phase concentration of an ingredient (or, through a mathematical relationship, the vapour pressure) that is part of the definition of ODC becomes partial volatility (or, through a mathematical relationship, the partial vapour pressure) due to ingredient(s) now being part of a mixture, and such partial quantities, including partial volatility or partial vapour pressure, are calculated from a mixture law by incorporating relative quantities of ingredients present in said mixture. Utilisation of Raoult's Law as the mixture law of choice to describe fragrance compositions is the most basic yet most practical embodiment. In more advanced embodiments, ODC for each ingredient in a fragrance composition is also being multiplied by an activity coefficient, which is quantity well known to a person skilled in the art of thermodynamics, physical chemistry, chemistry, chemical engineering, or related field. The activity coefficient for each ingredient is a correction factor for Raoult's Law (ideal) description of a mixture and describes the deviation in vapour-liquid equilibrium behaviour of a real and potentially non-ideal mixture compared to an ideal mixture. Activity coefficients for ingredients in ideal mixtures are equal to unity (1) by definition. Activity coefficients for ingredients in non-ideal mixtures can be calculated from well-established algorithms known in the art, which include but are not limited to UNIFAC or Modified UNIFAC.

This way, an ingredient performance in formulation calculated by the method 400 object of the present invention, yields maximum allowable gas phase (spatial) dilutions of constituent ingredients of a fragrance related to distance from the fragrance source while meeting or exceeding the minimum sensory performance criterion ('Iref' in the description of FIG. 1) for all constituent ingredients.

Figure 8:
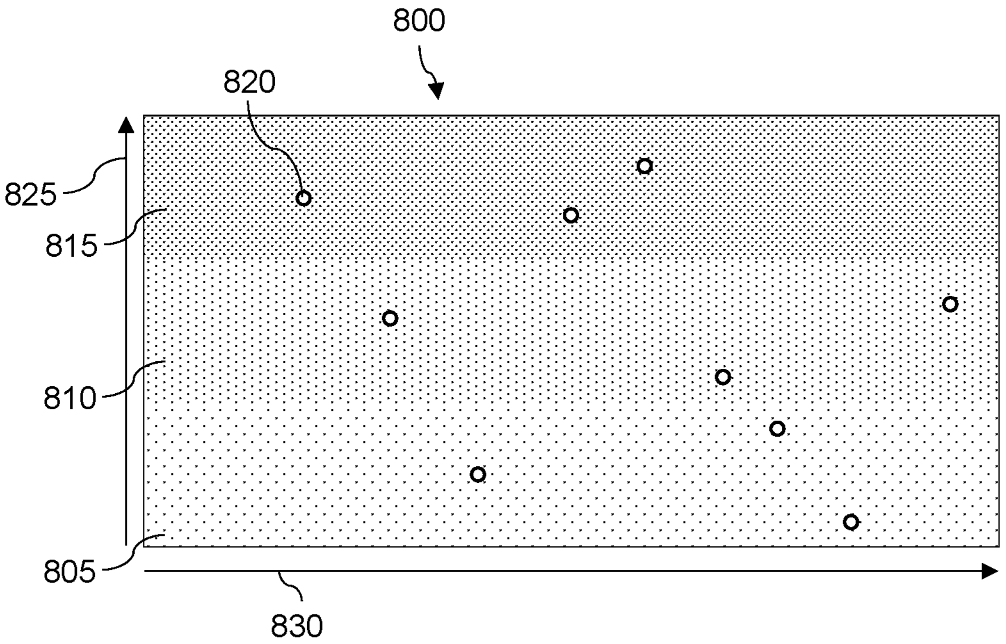
FIG. 8 represents, schematically, an interface representing the spatial reach of all ingredients in a fragrance composition on the vertical axis versus volatility of said ingredients on the horizontal axis.

FIG. 8 shows a graphical representation of a user interface 800 providing the metrics and analytics disclosed in the description above. Such an interface 800 may be used to assist users in fragrance design.

In this interface 800, ingredients 820 in a composition are ordered by increasing volatility 830 in the x-axis. The y-axis shows the spatial reach 825 for the ingredients in such a way that three distinct ingredient behaviours appear:

- a first behaviour 805 corresponds to ingredients being perceptible, at the minimum perception intensity level selected, close to the skin where the fragrance ingredient or composition is applied, typically within 5-10 cm from the skin,
- a second behaviour 810 corresponds to ingredients being perceptible, at the minimum perception intensity level selected, in the aura, the aura representing typically at least 5-10 cm away from the fragrance source but typically less than 50 cm away and certainly less than 1 metre away and
- a third behaviour 815 corresponds to ingredients being perceptible, at the minimum perception intensity level selected, in the trail, the trail representing the distances of at least 1 metre from the fragrance source, more preferably for some ingredients up to 2 metres, more preferably for some ingredients up to 4 metres and most preferably for some ingredients beyond 4 metres, the latter level of performance classified as 'room filling', a special case of the highest trail performance achievable.

It is hereby noted that the optimal performance in terms of distance may not be the same for all ingredients, which may depend on their olfactive descriptors and/or olfactive families to which they belong. The method object of this invention allows the persons skilled in the art of perfumery to predict performance of fragrance ingredients, including in fragrance compositions, and facilitate intelligent fragrance optimisation to achieve optimal or desired performance levels.

In terms of technical performance, the higher an ingredient is located along the y-axis, the more robustly it is performing in terms of spatial reach, or, the maximum downstream distance at which it can be perceived at the minimum requested sensory intensity level.

Such an interface 800 is represented at a given time in the dry down, which is the duration of time elapsed since application of the fragrance on the wearer. The data in this interface 800 could be calculated for several durations to show the impact of time upon the performance of the composition.

In particular embodiments, such as the one represented in FIG. 4, at least one ingredient digital identifier is associated, in a computer memory, to a descriptor representative of the scent of the corresponding ingredient, wherein the method further comprises a step of providing 415, upon a computer interface, at least one alternative ingredient digital identifier to at least one of the elected ingredient digital identifiers as a function of at least one descriptor associated to said elected ingredient digital identifier, as a way to optimise performance of the fragrance composition.

A descriptor can be representative of an ingredient olfactive family, for example. During the step of providing 415, a calculation is performed, for example by a computing system, in order to select ingredient identifiers different from the elected ingredient identifier, said selected ingredient identifiers having an at least one descriptor matching at least one of the descriptor of the elected ingredient identifier.

After this calculation has been performed, the result can be shown upon a computer interface to assist in fragrance design.

In particular embodiments, such as the one represented in FIG. 4, the step of providing 415 is achieved as a function of both at least one descriptor associated to said elected ingredient digital identifier and the computed value representative of a maximum downstream spatial distance for said ingredient digital identifier As such, preferably, the alternative ingredient identifiers are ranked according to their resistance to dilution, ODC, or any other performance indicator, or a combination of such performance indicators, based on the dose-response characteristics of ingredients.

For example, if a fragrance composition to be optimised contains Osyrol, which represents a sandalwood note in terms of olfactive description, potential replacement options, retrieved by the computing system executing the method object of this invention and presented to the user, will include such ingredients in the sandalwood family as Bacdanol, Javanol, Sandela, Ebanol, Sandalore, and Polysantol, listed here in no particular order. These ingredient replacement options will be displayed, either as tabular text or graphically, via the user interface and ranked in the order of above-mentioned performance indicators disclosed in the current invention.

Figure 5:
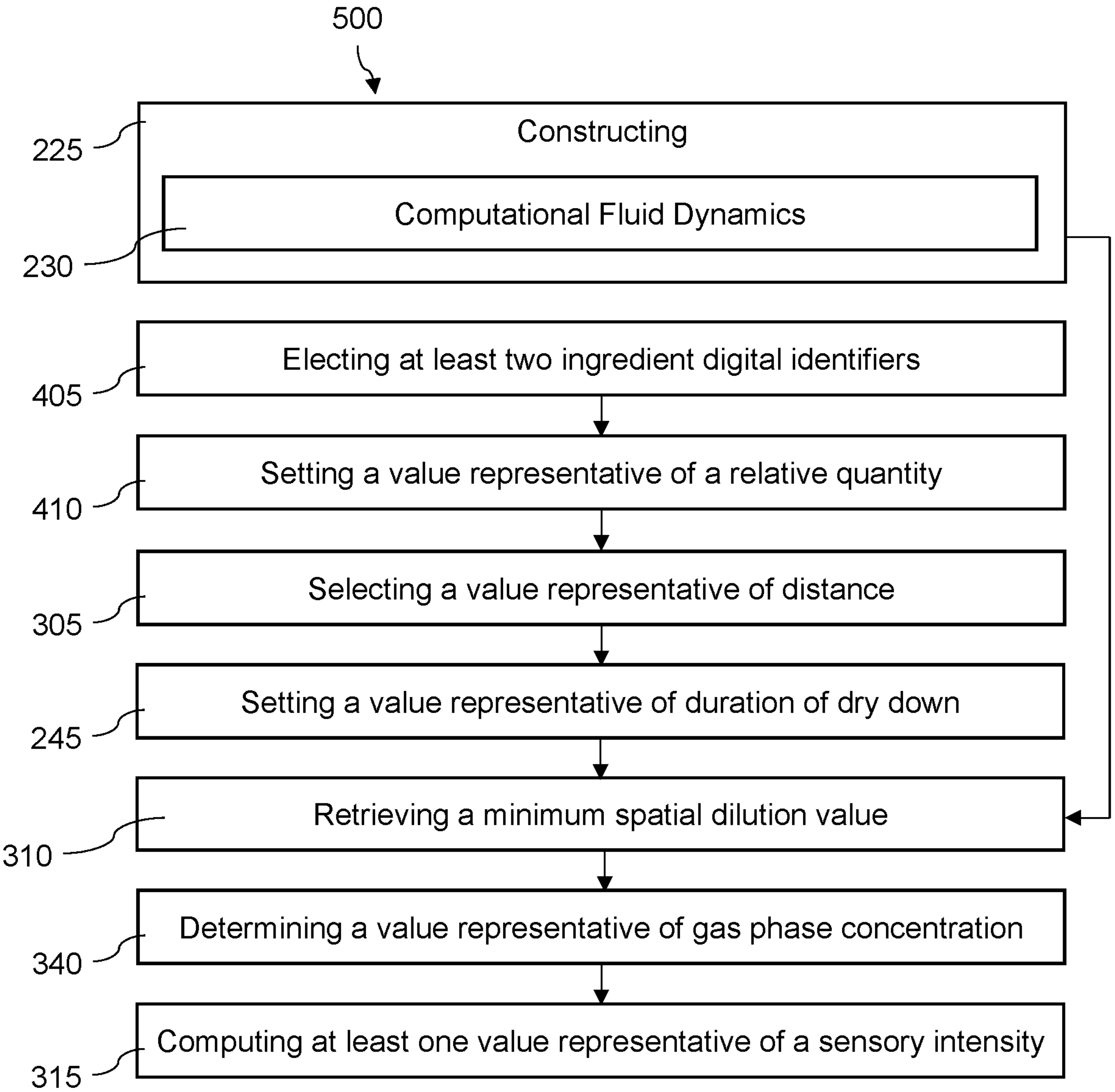
FIG. 5 represents, schematically and in the form of a flowchart, a fourth particular succession of steps of the method which is the object of the present invention.

FIG. 5 shows a particular succession of steps of a method which is the object of this invention. This fragrance composition spatial recognisability prediction method 500 to prepare a fragrance composition comprising said fragrance ingredient or composition, comprises the steps of:

- electing 405, upon a computer interface, at least two ingredient digital identifiers forming a fragrance source,
- setting 410, upon a computer interface, a value representative of a relative quantity of at least one said ingredient identified by said digital identifier,
- selecting 305, upon a computer interface, a value representative of a distance within a range of at least two distinct values and up to a maximum downstream distance from the fragrance source at which at least one ingredient presents a minimum sensory intensity level corresponding to a predetermined minimum psychophysical intensity for each said ingredient,
- retrieving 310, from an electronic storage, a minimum spatial dilution value associated with the selected distance,
- determining 340, by a computing system, a value representative of gas phase concentration of at least one said ingredient corresponding to the spatial dilution value retrieved and
- computing 315, by a computing system, for the selected value of distance, at least one value representative of a sensory intensity level as a function of a dose-response curve linking gas phase concentration to sensory intensity level.

The steps of electing 405 and setting 410 are similar to the corresponding steps disclosed in regards of FIG. 4.

The steps of selecting 305, retrieving 310 and computing 315 are similar to the corresponding steps disclosed in regards of FIG. 3.

The visualisation of fragrance compositions as shown in FIGS. 4 and 5 allows a person skilled in the art of perfumery, such as a perfumer, to readily identify the weak and the strong points of a composition in terms of olfactive impact, such as which olfactive tonalities are dominant at different times in the dry-down, and in terms of inherent olfactive performance properties of ingredients used in the composition, such as their performance at a distance in terms of spatial reach in the trail. Such a visualisation also allows a person skilled in the art to identify continuity of olfactive tonalities or notes, olfactively contrasting blocks of ingredients in the composition, as well as potential holes in the formula from the point of view of physico-chemical properties of constituent ingredients (for example, volatility) coupled with their olfactive character.

Figure 9:
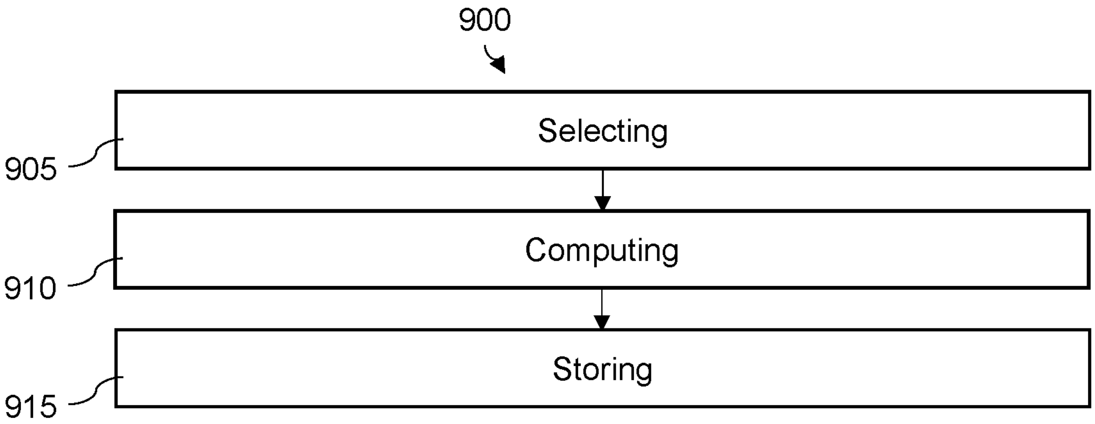
FIG. 9 represents, schematically and in the form of a flowchart, a fifth particular succession of steps of the method which is the object of the present invention.

FIG. 9 shows a particular succession of steps of a method which is the object of this invention. This ingredient digital identifier database enrichment method 900 comprises the steps of:

- selecting 905, by a computing system or computer interface, an ingredient digital identifier,
- computing 910, by a computing system, at least one of the following indicators:
  - an indicator representative of the spatial reach of the ingredient associated with the ingredient digital identifier as a function of a minimum perceived intensity level requested of said ingredient, wherein the minimum perceived intensity level is preferably selected during a step of selection of said minimum perceived intensity level, optionally as a function of the dose-response characteristics of said ingredient, optionally as a function of relative quantity of said ingredient in a fragrance composition, and optionally as a function of a dilution factor correlated to a given distance from the wearer for different parameters of fragrance wear (such as walking speed, quantity of liquid fragrance applied, and where on the body it is applied), wherein the dilution factor is preferably retrieved during a step of retrieving said dilution factor from a dilution factor database, said dilution factor database being preferably constituted during a step of constitution comprising a step of computational fluid dynamics simulation,
  - an indicator representative of the perceived intensity of the ingredient associated with the ingredient digital identifier as a function of a distance from said ingredient, wherein the distance is preferably selected during a step of selection of said distance, optionally as a function of the dose-response characteristics of said ingredient, optionally as a function of relative quantity of said ingredient in a fragrance composition, and optionally as a function of a dilution factor correlated to a given distance from the wearer for different parameters of fragrance wear (such as walking speed, quantity of liquid fragrance applied, and where on the body it is applied), wherein the dilution factor is preferably retrieved during a step of retrieving said dilution factor from a dilution factor database, said dilution factor database being preferably constituted during a step of constitution comprising a step of computational fluid dynamics simulation,
  - an indicator representative of the relative quantity of the ingredient associated with the ingredient digital identifier as a function of desired spatial reach of said ingredient from the fragrance source, optionally as a function of a minimum perceived intensity level requested of said ingredient, wherein the minimum perceived intensity level is preferably selected during a step of selection of said minimum perceived intensity level, optionally as a function of the dose-response characteristics of said ingredient, and optionally as a function of a dilution factor correlated to a given distance from the wearer for different parameters of fragrance wear (such as walking speed, quantity of liquid fragrance applied, and where on the body it is applied), wherein the dilution factor is preferably retrieved during a step of retrieving said dilution factor from a dilution factor database, said dilution factor database being preferably constituted during a step of constitution comprising a step of computational fluid dynamics simulation and/or
  - optionally, an indicator representative of a resistance to dilution of the ingredient associated with said ingredient digital identifier, said indicator being calculated as a function of a difference in perceived intensity between a nominal perceived intensity and the perceived intensity at a predetermined dilution factor,
- storing 915 the value of at least one computed indicator in correspondence to the ingredient digital identifier.

Figure 10:
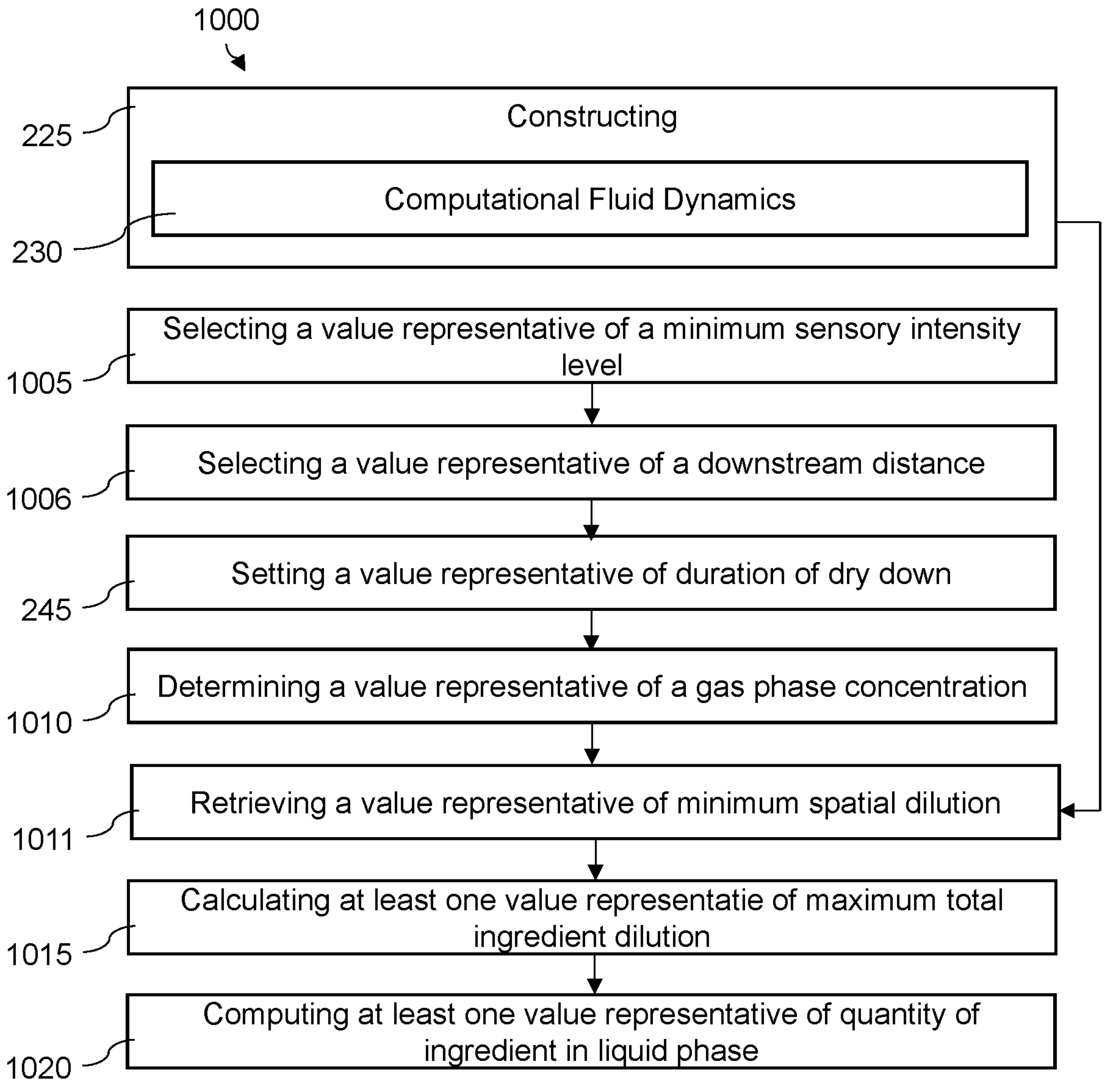
FIG. 10 represents, schematically and in the form of a flowchart, a sixth particular succession of steps of the method which is the object of the present invention.

FIG. 10 shows a particular succession of steps of a method which is the object of this invention. This fragrance ingredient or composition spatial recognisability prediction method 1000 to prepare a fragrance composition comprising said fragrance ingredient or composition, comprises the steps of:

- selecting 1005, upon a computer interface, a value representative of a minimum sensory intensity level to be achieved, corresponding to a predetermined minimum psychophysical intensity for the ingredient,
- selecting 1006, upon a computer interface, a value representative of a downstream distance from a fragrance source,
- determining 1010, by a computing system, a value representative of the gas phase concentration of the ingredient corresponding to the selected minimum sensory intensity level as a function of a dose response for said ingredient linking gas phase concentration to the selected minimum sensory intensity,
- retrieving 1011, from an electronic storage, a value of minimum spatial dilution as a function of the selected distance from the fragrance source,
- calculating 1015, by a computing system, at least one value representative of maximum total ingredient dilution as a function of the determined gas phase concentration for said ingredient and
- computing 1020, by a computing system, for at least one value representative of maximum total ingredient dilution calculated and at least one value representative of minimum spatial dilution retrieved for the selected distance, at least one value representative of a quantity of ingredient in liquid phase, so that the ingredient presents the minimum sensory intensity level as a function of the value of ingredient dilution at the predetermined distance.

The step of selecting 1005 can be performed in an analogous way to the step of selecting 205 described with regards to FIG. 2.

In particular embodiments, the method 1000 object of the present invention comprises a step of setting (not represented) a value representative of the predetermined distance. In such embodiments, the dilution is calculated as a function of the set value of distance from pre-calculated distance—dilution look-up table, stored for example in an electronic storage.

The step of determining 1010 can be performed in an analogous way to the step of determining 240 described with regards to FIG. 2.

The step of calculating 1015 is performed, for example, by a computing system configured to run a computer program executing an algorithm associating gas phase concentration to dilution as a function of distance. Such an algorithm is described, notably, in regard to FIG. 6.

The step of computing 1020 is performed, for example, by a computing system configured to run a computer program executing an algorithm associating dilution and minimum sensory intensity level to liquid phase quantity of an ingredient. The results of such an algorithm can be stored in an electronic storage accessed during this step of computing 1020.

Such an algorithm may use an evaporation rate linking the liquid phase quantity and duration of the dry down, which is the time elapsed from application of the liquid fragrance ingredient. Such an evaporation rate can be measured or modelled and stored into an electronic storage.

Evaporation rate is a consequence of mass transport dynamics, but it does not provide a complete liquid phase quantity to gas phase concentration correlation spatially.

The liquid phase quantity to gas phase concentration correlation is defined by momentum conservation and mass conservation equations, such as those used in the computational fluid dynamics calculation step. A table correlating distances to spatial dilution factors, from computational fluid dynamics, is a way to connect liquid phase to the gas phase in a distance-dependent way, utilising parameters of fragrance wear such as walking speed, quantity of liquid fragrance applied, and the location(s) on the body where the fragrance is applied.

An evaporation rate of an ingredient is used to perform the evaporation and compositional evolution simulation of the liquid phase of the fragrance in time. Then, the temporal compositional information is used in the different embodiments described herein.

In other embodiments (not represented), the present invention aims at a fragrance ingredient replacement method for the purposes of performance optimisation of fragrance compositions, which comprises the step of:

- selecting at least one ingredient to form a formula,
- computing a performance metric, such as disclosed in regards to FIGS. 2 to 10, such as the ODC, maximum spatial reach based on the ODC, perceived intensity at a given distance, resistance to dilution, or a combination of the aforementioned for at least one ingredient of the formula,
- determining, for at least one said ingredient, a list of olfactively related ingredients not present in the current formula presenting a preferable value of of chosen performance metrics or presenting an equal or inferior value of one chosen performance metric but at the same time a preferable value of another performance metric (such as cost for example), such list of ingredients optionally presented in a graphical interface showing relative values of the performance metrics compared to the original ingredient selected for replacement.

In other embodiments (not represented), the present invention aims at a fragrance ingredient relative quantity modification method in a fragrance composition, which comprises the step of:

- selecting at least one ingredient to form a formula,
- computing a performance metric, such as disclosed in regards to FIGS. 2 to 10, such as the ODC, maximum spatial reach based on the ODC, perceived intensity at a given distance, resistance to dilution, or a combination of the aforementioned for at least one ingredient of the formula,
- determining, for at least one said ingredient, a recommendation of increase or decrease its relative quantity in a composition in order to achieve a target value for the performance metric with the aim to the fragrance composition.

Figure 13:
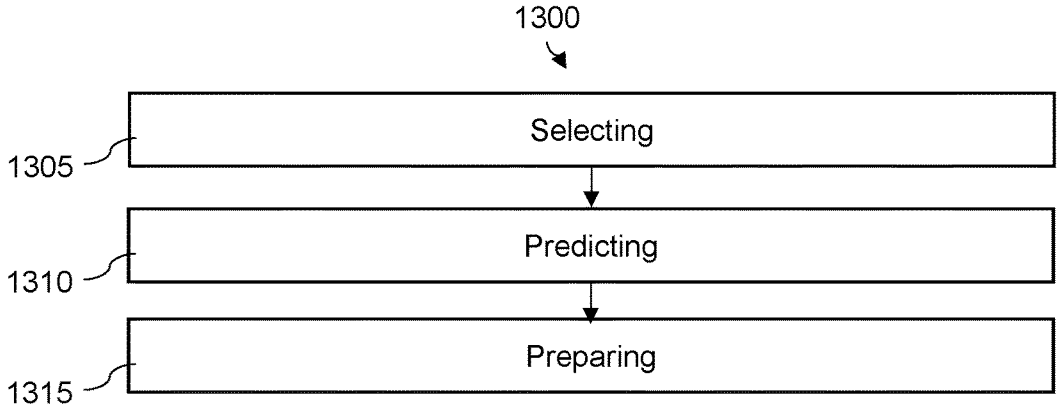
FIG. 13 represents, schematically and in the form of a flowchart, a seventh particular succession of steps of the method which is the object of the present invention.

FIG. 13 shows, schematically, a particular embodiment of the method 1300 object of the present invention. This fragrance 1300 composition preparation method, characterised in that it comprises:

- a step 1305 of selecting, upon a computer interface, at least one ingredient digital identifier to form a fragrance composition digital representation,
- a step 1310 of predicting, by a computing device, a spatial recognisability for at least one selected ingredient digital identifier according to a fragrance composition spatial recognisability prediction method, 200, 300, 400, 500 and/or 1000, according to any embodiment disclosed above and
- a step 1315 of preparing a fragrance composition as a function of the fragrance composition digital representation.

The step 1305 of selecting may be performed similarly to the step 205 of selecting or any other similar step disclosed above. During this step 1305 of selecting, a user or computer program selects at least one identifier representative of a physical ingredient digital to form a fragrance composition represented by a digital representation, such as an identifier or graphic representation.

The step 1310 of predicting may be performed by any embodiment of the method, 200, 300, 400, 500 and/or 1000, disclosed above.

The step 1315 of preparing may be performed by any one ingredient digital identifier composition manufacturing technique known to a person skilled in the art.

Figure 15:
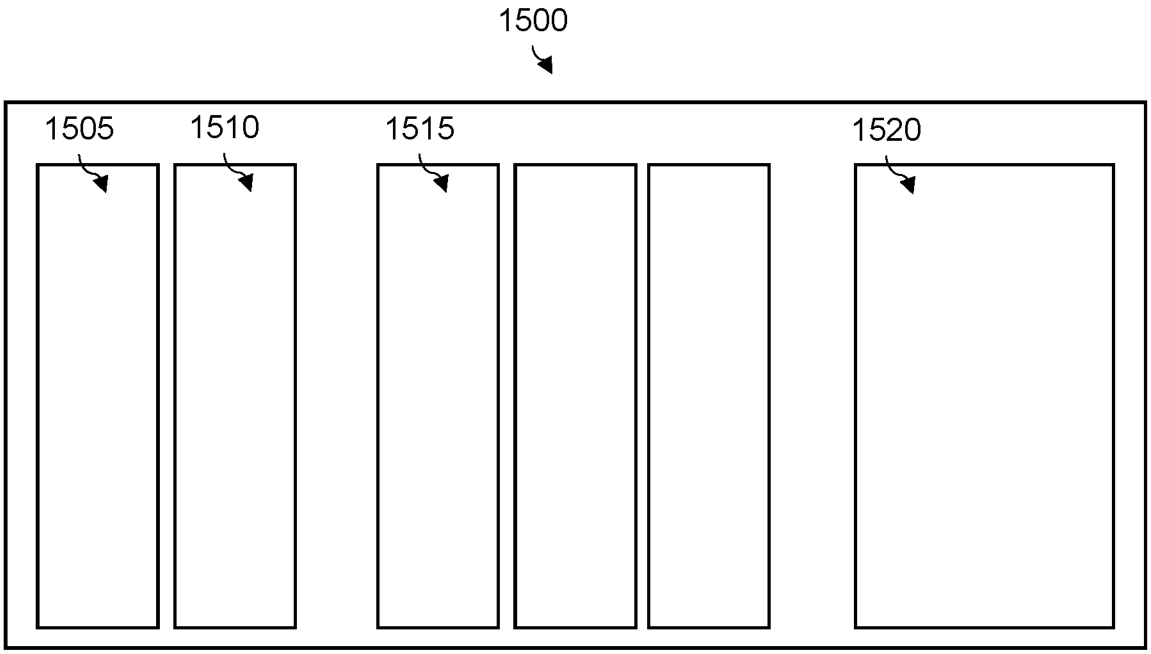
FIG. 15 represents, schematically, an interface of a software implementing the method object of the present invention.

FIG. 15 shows, schematically, an example of a user interface 1500 of a software implementing a method, 200, 300, 400 and/or 1000, object of the present invention. This user interface 1500 comprises:

- an ingredient digital identifier list 1505 that can be updated by adding or removing ingredient digital identifiers,
- an associated ingredient quantity list 1510 that can be updated and show either relative or absolute quantities for each ingredient,
- a customisable performance space 1515, showing any one key performance indicator obtained using any method, 200, 300, 400 and/or 1000, object of the present—sur an indicator may be a maximum distance for perception at specific times from fragrance release,
- an optimisation suggestion space 1520, showing ways in which the designed fragrance may be optimised according to the performance indicators associated to the ingredients—such optimisations may correspond to a change in quantity or ingredient digital identifier, for example.

The invention claimed is:

1. Fragrance composition preparation method to prepare a fragrance composition comprising a fragrance ingredient associated with an ingredient digital identifier, comprising the steps of:

selecting, upon a computer interface, at least one ingredient digital identifier to form a fragrance composition digital representation;

predicting, by a computing device, a spatial recognisability for at least one selected ingredient digital identifier according to a fragrance composition spatial recognisability prediction method comprising:

selecting, upon a computer interface, a measurable value representative of at least one of the following parameters:

a minimum sensory intensity level, corresponding to a predetermined minimum psychophysical intensity for the ingredient, a maximum distance, corresponding to a distance at which the ingredient is to be perceived at a minimum predetermined psychophysical intensity level or a quantity of the ingredient in liquid phase, wherein the selected value is selected within a range of at least two distinct values, computing, by a computing system, a value representative of at least one of the following parameters:

a minimum sensory intensity level, corresponding to a predetermined minimum psychophysical intensity for the ingredient, a maximum distance, corresponding to a distance at which the ingredient is to be perceived at a minimum sensory intensity level selected or set by default, or a quantity of the ingredient in liquid phase, wherein the computed value is representative of a parameter other than the parameter associated with the selected value and wherein a value for the parameter neither selected nor computed is set to a default value, said ingredient digital identifier corresponding to a physical ingredient to be used within a fragrance composition to be prepared as a function of the computed and selected values, and a step of providing, by a computing system, a preparable fragrance composition digital representation representative of a physical fragrance composition comprising said physical ingredient, as a function of the computed and selected values; and preparing a fragrance composition as a function of the fragrance composition digital representation, wherein preparing the fragrance composition comprises altering a quantity associated with the ingredient or an identity of the ingredient relative to the fragrance composition digital representation.

2. Fragrance composition preparation method according to claim 1, comprising the steps of:

selecting, upon a computer interface, a value representative of a minimum requested sensory intensity level, corresponding to a desirable predetermined perceived minimum psychophysical intensity for the ingredient, said value being selected within a range of at least two distinct values, determining, by a computing system, a value representative of a minimum gas phase concentration of the ingredient corresponding to the selected minimum sensory intensity level as a function of a dose-response curve linking gas phase concentration to the selected minimum sensory intensity, calculating, by a computing system, a maximum total acceptable ingredient dilution, for both in gas and liquid phases of the fragrance, as a function of the determined minimum gas phase concentration and computing, by a computing system, at least one value representative of a distance from the fragrance source, up to a maximum distance from the fragrance source, at which the ingredient presents at least the minimum sensory intensity level selected as a function of the maximum total ingredient dilution calculated, said computing step comprising a step of retrieving, from an electronic storage, at least one value representative of the minimum spatial dilution for an ingredient in the gas phase corresponding to a predetermined downstream distance from the fragrance source.

3. Method according to claim 2, which further comprises, prior to the step of retrieving, a step of constructing a minimum spatial dilution electronic storage, said step of constructing matching minimum spatial dilution values to at least one distance from a fragrance source value and at least one of the following indicators:

an indicator representative of an incoming air flow velocity incident upon the fragrance source comprising said ingredient, an indicator representative of an ingredient or fragrance composition application surface area, an indicator representative of simulation parameters for the shape of a human body and/or an indicator representative of area location on a human body upon which the ingredient or fragrance composition is applied, said step of constructing comprising a step of computational fluid dynamics simulation configured to calculate said spatial dilution values at predetermined downstream distances from the source.

4. Method according to claim 3, which further comprises a step of setting a value representative of a duration of dry down of an ingredient, the step of computing of a value representative of a distance from the fragrance source being achieved as a function of the duration of dry down set.

5. Method according to claim 2, which further comprises a step of setting a value representative of a duration of dry down of an ingredient, the step of computing of a value representative of a distance from the fragrance source being achieved as a function of the duration of dry down set.

6. Fragrance composition preparation method according to claim 1, comprising the steps of:

selecting, upon a computer interface, a value representative of a distance within a range of at least two distinct values and up to a maximum downstream distance from the fragrance source at which the ingredient presents a minimum sensory intensity level corresponding to a predetermined minimum psychophysical intensity for the ingredient, retrieving, from an electronic storage, a minimum spatial dilution value associated with the selected distance, determining, by a computing system, a value representative of gas phase concentration of the ingredient corresponding to the spatial dilution value retrieved and computing, by a computing system, for the selected value of distance, at least one value representative of a sensory intensity level as a function of a dose-response curve linking gas phase concentration to sensory intensity level.

7. Fragrance composition preparation method according to claim 1, comprising the steps of:

selecting, upon a computer interface, a value representative of a minimum sensory intensity level to be achieved, corresponding to a predetermined minimum psychophysical intensity for the ingredient, selecting, upon a computer interface, a value representative of a downstream distance from a fragrance source, determining, by a computing system, a value representative of the gas phase concentration of the ingredient corresponding to the selected minimum sensory intensity level as a function of a dose response for said ingredient linking gas phase concentration to the selected minimum sensory intensity, retrieving, from an electronic storage, a value of minimum spatial dilution as a function of the selected distance from the fragrance source, calculating, by a computing system, at least one value representative of maximum total ingredient dilution as a function of the determined gas phase concentration for said ingredient and computing, by a computing system, for at least one value representative of maximum total ingredient dilution calculated and at least one value representative of minimum spatial dilution retrieved for the selected distance, at least one value representative of a quantity of ingredient in liquid phase, so that the ingredient presents the minimum sensory intensity level as a function of the value of ingredient dilution at the predetermined distance.

8. Fragrance composition preparation method according to claim 1, comprising the steps of:

electing, upon a computer interface, at least two ingredient digital identifiers to form a fragrance source, setting, upon a computer interface, a value representative of a relative quantity of at least one said ingredient identified by said digital identifier, selecting, upon a computer interface, a value representative of a minimum requested sensory intensity level, corresponding to a desirable predetermined perceived minimum psychophysical intensity for at least one ingredient, said value being selected within a range of at least two distinct values, determining, by a computing system, a value representative of a minimum gas phase concentration for each said ingredient corresponding to the selected minimum sensory intensity level as a function of a dose-response curve linking gas phase concentration to the selected minimum sensory intensity, calculating, by a computing system, a maximum total ingredient dilution, for both in gas and liquid phases of the fragrance, as a function of the determined minimum gas phase concentration, for each said ingredient and computing, by a computing system, at least one value representative of a distance from the fragrance source, up to a maximum distance from the fragrance source, at which at least one ingredient presents at least the minimum sensory intensity level selected as a function of the maximum total ingredient dilution calculated.

9. Method according to claim 8, in which at least one ingredient digital identifier is associated, in a computer memory, to a descriptor representative of the scent of the corresponding ingredient, wherein the method further comprises a step of providing (415), upon a computer interface, at least one alternative ingredient digital identifier to at least one of the elected ingredient digital identifiers as a function of at least one descriptor associated to said elected ingredient digital identifier.

10. Method according to claim 9, in which the step of providing is achieved as a function of both at least one descriptor associated to said elected ingredient digital identifier and the computed value representative of a maximum downstream spatial distance for said ingredient digital identifier.

11. Fragrance composition preparation method according to claim 1, comprising the steps of:

electing, upon a computer interface, at least two ingredient digital identifiers forming a fragrance source, setting, upon a computer interface, a value representative of a relative quantity of at least one said ingredient identified by said digital identifier, selecting, upon a computer interface, a value representative of a distance within a range of at least two distinct values and up to a maximum downstream distance from the fragrance source at which at least one ingredient presents a minimum sensory intensity level corresponding to a predetermined minimum psychophysical intensity for each said ingredient, retrieving, from an electronic storage, a minimum spatial dilution value associated with the selected distance, determining, by a computing system, a value representative of gas phase concentration of at least one said ingredient corresponding to the spatial dilution value retrieved and computing, by a computing system, for the selected value of distance, at least one value representative of a sensory intensity level as a function of a dose-response curve linking gas phase concentration to sensory intensity level.

12. The fragrance composition preparation method of claim 1, further comprising:

generating an optimisation suggestion comprising an indication of at least one of a change in quantity associated with the ingredient, or a change in an identity of the ingredient based on a performance indicator associated with the ingredient.

13. The fragrance composition preparation method of claim 12, wherein preparing the fragrance composition comprises altering the quantity associated with the ingredient or the identity of the ingredient based on the optimisation suggestion.

* * * * *